(12) United States Patent
Jaworek et al.

(10) Patent No.: US 7,250,481 B2
(45) Date of Patent: Jul. 31, 2007

(54) METHOD FOR THE PRODUCTION OF ESTERS OF POLYALCOHOLS

(75) Inventors: Thomas Jaworek, Kallstadt (DE); Thomas Daniel, Waldsee (DE); Lothar Wolf, Torno (DE); Rainer Koeniger, Mannheim (DE); Reinhold Schwalm, Wachenheim (DE); Gabriele Hartmann, Hockenheim (DE); Stefan Wickel, Bissersheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/514,569

(22) PCT Filed: Jun. 6, 2003

(86) PCT No.: PCT/EP03/05940

§ 371 (c)(1),
(2), (4) Date: Dec. 1, 2004

(87) PCT Pub. No.: WO03/104299

PCT Pub. Date: Dec. 18, 2003

(65) Prior Publication Data

US 2005/0176910 A1   Aug. 11, 2005

(30) Foreign Application Priority Data

Jun. 11, 2002   (DE) ................. 102 25 943

(51) Int. Cl.
C08F 22/10 (2006.01)
(52) U.S. Cl. ............. 526/321; 526/317.1; 526/318.4; 526/318.43; 526/323.1; 526/323.2
(58) Field of Classification Search ............ 526/317.1, 526/318.4, 318.43, 323.1, 323.2, 321; 560/205
See application file for complete search history.

(56) References Cited

U.S. PATENT DOCUMENTS 3,380,831 A * 4/1968 Cohen .................. 430/288.1
4,076,663 A * 2/1978 Masuda et al. .......... 525/54.31
4,187,383 A * 2/1980 Cowherd et al. ........... 560/224
4,295,987 A * 10/1981 Parks ......................... 252/194
4,859,792 A * 8/1989 Powanda et al. ........... 560/204
5,198,574 A * 3/1993 Ritter et al. ................. 560/224
5,298,582 A * 3/1994 Brusson et al. ............. 526/262
5,350,877 A * 9/1994 Ritter et al. ................. 560/224
5,356,754 A * 10/1994 Kushi et al. .............. 430/288.1
5,506,324 A * 4/1996 Gartner et al. .......... 526/318.41
5,574,121 A * 11/1996 Irie et al. ................ 526/318.44
5,648,518 A * 7/1997 Ritter et al. ................. 560/224
5,661,220 A * 8/1997 Faul et al. ................... 525/384
5,821,383 A * 10/1998 Haussling et al. .......... 560/205
6,063,957 A * 5/2000 Koniger et al. ............. 560/218
6,107,429 A * 8/2000 Sojka ....................... 526/323.2
6,395,830 B1 * 5/2002 Jonas et al. ................. 525/102
6,673,885 B1 * 1/2004 Shibata et al. .......... 526/318.41
2002/0193492 A1 * 12/2002 Wilson ....................... 524/437
2003/0045847 A1 * 3/2003 Whitmore et al. .......... 604/368

FOREIGN PATENT DOCUMENTS

| EP | 0 331 845 | 9/1989 |
|----|-----------|--------|
| EP | 0 874 014 | 10/1998 |
| WO | 93 21237 | 10/1993 |
| WO | 98 47951 | 10/1998 |
| WO | 01 10920 | 2/2001 |
| WO | 01 14438 | 3/2001 |
| WO | 01 41818 | 6/2001 |
| WO | 01 56625 | 8/2001 |

* cited by examiner

Primary Examiner—David W. Wu
Assistant Examiner—M. Bernshteyn
(74) Attorney, Agent, or Firm—Oblon, Spivak, McClelland, Maier & Neustadt, P.C.

(57) ABSTRACT

Unsaturated acids are esterified with polyalcohols. The resulting reaction mixtures have utility.

30 Claims, No Drawings

METHOD FOR THE PRODUCTION OF ESTERS OF POLYALCOHOLS

CROSS REFERENCES TO RELATED APPLICATIONS

This application is a national stage application of International Patent Application No. PCT/EP03/05940, filed on Jun. 6, 2003, and claims priority to German Patent Application No. 102 25 943.7, filed on Jun. 11, 2002, both of which are incorporated herein by reference in their entireties.

The present invention relates to a simplified process for esterifying unsaturated acids with polyalcohols and to the use of reaction mixtures thus obtainable.

Swellable hydrogel-forming addition polymers, known as superabsorbent polymers or SAPs, are known from the prior art. They are networks of flexible hydrophilic addition polymers, which can be both ionic and nonionic in nature. They are capable of absorbing and binding aqueous fluids by forming a hydrogel and therefore are preferentially used for manufacturing tampons, diapers, sanitary napkins, incontinence articles, training pants for children, insoles and other hygiene articles for the absorption of body fluids. Superabsorbents are also used in other fields of technology where fluids, especially water or aqueous solutions, are absorbed. These fields include for example storage, packaging, transportation (packaging material for water-sensitive articles, for example flower transportation, shock protection); food sector (transportation of fish, fresh meat; absorption of water, blood in fresh fish/meat packs); medicine (wound plasters, water-absorbent material for burn dressings or for other weeping wounds), cosmetics (carrier material for pharmaceuticals and medicaments, rheumatic plasters, ultrasound gel, cooling gel, cosmetic thickeners, sunscreen); thickeners for oil/water or water/oil emulsions; textiles (gloves, sportswear, moisture regulation in textiles, shoe inserts); chemical process industry applications (catalyst for organic reactions, immobilization of large functional molecules (enzymes), adhesive for agglomerations, heat storage media, filtration aids, hydrophilic component in polymer laminates, dispersants, liquefiers); building and construction, installation (powder injection molding, clay-based renders, vibration-inhibiting medium, assistants in relation to tunneling in water-rich ground, cable sheathing); water treatment, waste treatment, water removal (deicers, reusable sandbags); cleaning; agriculture industry (irrigation, retention of meltwater and dew precipitates, composting additive, protection of forests against fungal and insect infestation, delayed release of active ingredients to plants); fire protection (flying sparks)(covering houses or house walls with SAP gel, since water has a very high heat capacity, ignition can be prevented; spraying of SAP gel in the case of fires such as for example forest fires); coextrusion agent in thermoplastic polymers (hydrophilicization of multilayer films); production of films and thermoplastic moldings capable of absorbing water (for example agricultural films capable of storing rain and dew water); SAP-containing films for keeping fresh fruit and vegetables which can be packed in moist films; the SAP stores water released by the fruit and vegetables without forming condensation droplets and partly reemits the water to the fruit and vegetables, so that neither fouling nor wilting occurs; SAP-polystyrene coextrudates for example for food packs such as meat, fish, poultry, fruit and vegetables); carrier substance in active-ingredient formulations (drugs, crop protection). Within hygiene articles, superabsorbents are generally positioned in an absorbent core which comprises other materials, including fibers (cellulose fibers), which act as a kind of liquid buffer to intermediately store the spontaneously applied liquid insults and are intended to ensure efficient channelization of the body fluids in the absorbent core toward the superabsorbent.

The current trend in diaper design is toward ever thinner constructions having a reduced cellulose fiber content and an increased hydrogel content. The trend toward ever thinner diaper constructions has substantially changed the performance profile required of the water swellable hydrophilic polymers over the years. Whereas at the start of the development of highly absorbent hydrogels it was initially solely the very high swellability on which interest focused, it was subsequently determined that the ability of the superabsorbent to transmit and distribute fluid is also of decisive importance. It has been determined that conventional superabsorbents greatly swell at the surface on wetting with liquid, so that transportation of liquid into the particle interior is substantially compromised or completely prevented. This trait of superabsorbents is known as gel blocking. The greater amount of polymer per unit area in the hygiene article must not cause the swollen polymer to form a barrier layer to subsequent fluid. A product having good transportation properties will ensure optimal utilization of the entire hygiene article. This prevents the phenomenon of gel blocking, which in the extreme case will cause the hygiene article to leak. Fluid transmission and distribution is thus of decisive importance with regard to the initial absorption of body fluids.

Good transportation properties are possessed for example by hydrogels having high gel strength in the swollen state. Gels lacking in strength are deformable under an applied pressure, for example pressure due to the bodyweight of the wearer of the hygiene article, and clog the pores in the SAP/cellulose fiber absorbent and so prevent continued absorption of fluid. Enhanced gel strength is generally obtained through a higher degree of crosslinking, although this reduces retention performance. An elegant way to enhance gel strength is surface postcrosslinking. In this process, dried superabsorbents having an average crosslink density are subjected to an additional crosslinking step. Surface postcrosslinking increases the crosslink density in the sheath of the superabsorbent particle, whereby the absorbency under load is raised to a higher level. Whereas the absorption capacity decreases in the superabsorbent particle sheath, the core has an improved absorption capacity (compared to the sheath) owing to the presence of mobile polymer chains, so that sheath construction ensures improved fluid transmission without occurrence of the gel blocking effect. It is perfectly desirable for the total capacity of the superabsorbent to be occupied not spontaneously but with time delay. Since the hygiene article is generally repeatedly insulted with urine, the absorption capacity of the superabsorbent should sensibly not be exhausted after the first disposition.

Highly swellable hydrophilic hydrogels are especially polymers of (co)polymerized hydrophilic monomers, graft (co)polymers of one or more hydrophilic monomers on a suitable grafting base, crosslinked cellulose or starch ethers, crosslinked carboxymethylcellulose, partially crosslinked polyalkylene oxide or natural products which swell in aqueous fluids, for example guar derivatives. Such hydrogels are used as products which absorb aqueous solutions to produce diapers, tampons, sanitary napkins and other hygiene articles, but also as water-retaining agents in market gardening.

To improve the performance properties, for example Rewet in the diaper and AUL, highly swellable hydrophilic hydrogels are generally surface or gel postcrosslinked. This postcrosslinking is known per se to one skilled in the art and is preferably effected in aqueous gel phase or as surface postcrosslinking of the ground and classified polymer particles.

WO 93/21237 discloses (meth)acrylates of alkoxylated $C_2$–$C_{10}$ polyhydric hydrocarbons that are useful as crosslinkers. These can be used as mixtures with by-products from the production process.

The disadvantage with these compounds is that costly and inconvenient cleaning operations are needed for at least partial removal of starting materials and by-products; the crosslinkers used in the reference cited have an acrylic acid content of less than 0.1% by weight.

The production of such higher (meth)acrylic esters by acid-catalyzed esterification of (meth)acrylic acid with the corresponding alcohols in the presence of an inhibitor/inhibitor system and in the presence or absence of a solvent such as benzene, toluene or cyclohexane is common knowledge.

Since the formation of the ester from (meth)acrylic acid and alcohol is known to be based on an equilibrium reaction, it is customary to use one starting material in excess and/or to remove the esterification water formed and/or the target ester from the equilibrium in order that commercial conversions may be obtained.

Therefore, in the production of higher (meth)acrylic esters, it is customary to remove the water of reaction and to use an excess of (meth)acrylic acid.

U.S. Pat. No. 4,187,383 describes an esterification process of (meth)acrylic acid with organic polyols at a reaction temperature of from 20 to 80° C. using an equivalent excess of from 2:1 to 3:1.

The disadvantage of this process is that the low reaction temperature means that the reaction times are up to 35 hours and that excess acid in the reaction mixture is removed by neutralization followed by phase separation.

WO 2001/14438 (Derwent Abstract No. 2001-191644/19) and WO 2001/10920 (Chemical Abstracts 134:163502) describe processes for esterifying (meth)acrylic acid with polyalkylene glycol monoalkyl ethers in a ratio of 3:1–50:1 in the presence of acids and polymerization inhibitors and, after deactivation of the acidic catalyst, copolymerization of the residue of (meth)acrylic ester and (meth)acrylic acid at pH 1.5–3.5, and also the use of said residue as a cement additive.

The disadvantage with these processes is that it is restricted to polyalkylene glycol monoalkyl ethers, that the catalyst has to be deactivated and that such copolymers cannot be used as crosslinkers for hydrogels since they only have one functionality.

It is an object of the present invention to simplify processes for preparing substances which are useful as radical crosslinkers for superabsorbents.

We have found that this object is achieved by a process for preparing an ester F of a polyalcohol A with at least one ethylenically unsaturated carboxylic acid B by steps which include a) reacting a polyalcohol A with at least one ethylenically unsaturated carboxylic acid B in the presence of at least one esterification catalyst C and of at least one polymerization inhibitor D and also optionally of a water-azeotroping solvent E to form an ester F,
b) optionally removing some or all of the water formed in a) from the reaction mixture during and/or after a),
f) optionally neutralizing the reaction mixture,
h) optionally removing any solvent E by distillation and/or
i) stripping with a reaction-inert gas, wherein
said polyalcohol A has at least two hydroxyl functions,
the molar excess of said ethylenically unsaturated carboxylic acid B to said polyalcohol A per hydroxyl group to be esterified in A is at least 1.05:1, and
the optionally neutralized carboxylic acid B in the reaction mixture obtained after the last step substantially remains in said reaction mixture.

The molar excess of B to A, per hydroxyl group (in the polyalcohol A) which is to be esterified, is at least 1.05:1, preferably at least 1.1:1, more preferably at least 1.25:1, most preferably at least 1.5:1 and especially at least 2.5:1.

In a preferred embodiment, B is used in an excess of for example greater than 5:1, preferably greater than 10:1, more preferably greater than 20:1, most preferably greater than 50:1, especially greater than 75:1 and specifically greater than 100:1.

The esterification products thus obtainable can be used as radical crosslinkers in hydrogels substantially without further purification, specifically without substantial removal of the excess of carboxylic acid B and of the esterification catalyst C.

Unless otherwise mentioned, crosslinking as used herein is to be understood as meaning radical crosslinking (gel crosslinking; internal crosslinking; cross-linking together of linear or lightly crosslinked polymer). This crosslinking can take place via free-radical or cationic polymerization mechanisms or other mechanisms, for example Michael addition, esterification or transesterification mechanisms, but is preferably effected by free-radical polymerization.

Hydrogel-forming polymers capable of absorbing aqueous fluids preferably are capable of absorbing at least their own weight and more preferably 10 times their own weight of distilled water and they are preferably capable of achieving this absorption even under a pressure of 0.7 psi.

Useful polyalcohols A for the purposes of the present invention include compounds having at least two hydroxyl (—OH) functions and more preferably at least three, yet more preferably from three to ten, most preferably from three to six and especially from three to four.

The polyalcohols can be aliphatic, cycloaliphatic or aromatic, preferably aliphatic or cycloaliphatic and most preferably aliphatic, straight-chain or branched and optionally substituted by functional groups.

The polyalcohols generally have from two to 50 and preferably from three to 40 carbon atoms.

The molecular weight of the polyalcohols which can be used is generally, unless otherwise stated, below 5000 g/mol, preferably below 2500 g/mol, more preferably below 1500 g/mol, most preferably below 1000 g/mol and especially below 800 g/mol.

Preferred polyalcohols A are polyols, functionalized polyols, alkoxylated polyols, sugar alcohols, partially alkoxylated sugar alcohols, polyetherols, polyesterols, partially or fully alkoxylated polyesterols and partially or fully hydrolyzed, alkoxylated polyesterols.

Examples of polyols are trimethylolbutane, trimethylolpropane, trimethylolethane, neopentylglycol, neopentylglycol hydroxypivalate, pentaerythritol, glycerol, 1,2-ethylene glycol, 1,2-propylene glycol, 2-ethyl-1,3-propanediol, 2-methyl-1,3-propanediol, hydroquinone, bisphenol A, bisphenol F, bisphenol B, 2,2-bis(4-hydroxycyclohexyl)propane, 1,1-, 1,2-, 1,3- and 1,4-cyclohexanedimethanol, 1,2-, 1,3- or 1,4-cyclohexanediol, but-2-ene-1,14-diol and but-2-yne-1,4-diol.

The polyols may bear additional functionalities, for example ether functions (—O—), carboxyl functions (—COOH) or $C_1$–$C_4$-alkoxycarbonyl functions (ester groups), the term $C_1$–$C_4$-alkyl as used herein denoting methyl, ethyl, iso-propyl, n-propyl, n-butyl, iso-butyl, sec-butyl or tert-butyl.

Examples of such functionalized polyols are ditrimethylolpropane, dipentaerythritol, dimethylolpropionic acid, dimethylolbutyric acid, trimethylol acetic acid, hydroxypivalic acid and the 2-hydroxyethyl or $C_1$–$C_4$-alkyl esters of said acids.

Preferred polyols are those of the formula (I):

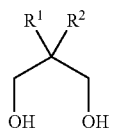

(I)

where
$R^1$ and $R^2$ are independently hydrogen, $C_1$–$C_{10}$-alkyl, preferably $C_1$–$C_4$-alkyl, $C_1$–$C_{10}$-hydroxyalkyl, preferably hydroxy $C_1$–$C_4$-alkyl, carboxyl or $C_1$–$C_4$-alkyloxycarbonyl, preferably hydrogen, hydroxymethyl and $C_1$–$C_4$-alkyl and more preferably hydroxymethyl and $C_1$–$C_4$-alkyl.

The alkyl radicals may each be straight-chain or branched.

Examples of $R^1$ and $R^2$ are hydrogen, methyl, ethyl, iso-propyl, n-propyl, n-butyl, iso-butyl, sec-butyl, tert-butyl, n-pentyl, n-hexyl, n-heptyl, n-octyl, n-decyl, hydroxymethyl, carboxyl, methoxycarbonyl, ethoxycarbonyl or n-butoxycarbonyl, preferably hydrogen, hydroxymethyl, methyl and ethyl, more preferably hydroxymethyl, methyl and ethyl.

Particularly preferred polyhydric alcohols of the formula (I) are trimethylolbutane, trimethylolpropane, trimethylolethane, neopentylglycol, pentaerythritol, 2-ethyl-1,3-propanediol, 2-methyl-1,3-propanediol, 1,3-propanediol, dimethylolpropionic acid, methyl dimethylolpropionate, ethyl dimethylolpropionate, dimethylolbutyric acid, methyl dimethylolbutyrate or ethyl dimethylolbutyrate, preference being given to neopentylglycol, trimethylolpropane, pentaerythritol and dimethylolpropionic acid, particular preference being given to neopentylglycol, trimethylolpropane and pentaerythritol and most preference being given to trimethylolpropane and pentaerythritol.

Examples of sugar alcohols are sorbitol, mannitol, malitol, Isomalt, diglycerol, threitol, erythritol, adonitol (ribitol), arabitol (lyxitol), xylitol and dulcitol (galactitol).

Examples of polyetherols are polytetrahydrofuran having a molar mass in the range from 162 to 2000, preferably in the range from 162 to 1458, more preferably in the range from 162 to 1098, yet more preferably in the range from 162 to 738 and most preferably in the range from 162 to 378, poly-1,3-propanediol and poly-1,2-propanediol having a molar mass in the range from 134 to 1178, preferably in the range from 134 to 888, more preferably in the range from 134 to 598 and most preferably in the range from 134 to 308, polyethylene glycol having a molar mass in the range from 106 to 898, preferably in the range from 106 to 458, more preferably in the range from 106 to 400 and yet more preferably in the range from 106 to 235 and most preferably diethylene glycol, triethylene glycol and tetraethylene glycol.

Useful polyesterols include for example polyesterols preparable by esterification of polycarboxylic acids, preferably dicarboxylic acids, with the abovementioned polyols.

The starting materials for such polyesterols are known to one skilled in the art. Polycarboxylic acids whose use may be preferable are oxalic acid, maleic acid, fumaric acid, succinic acid, glutaric acid, adipic acid, sebacic acid, dodecanedioc acid, o-phthalic acid, isophthalic acid, terephthalic acid, trimellitic acid, azelaic acid, 1,4-cyclohexanedicarboxylic acid or tetrahydrophthalic acid, their isomers and hydrogenation products and also esterifiable derivatives, such as anhydrides or dialkyl esters, for example $C_1$–$C_4$-alkyl esters, preferably methyl, ethyl or n-butyl esters.

Useful hydroxyl-containing carboxylic acids or lactones include 4-hydroxybenzoic acid, 6-hydroxy-2-napthoic acid, pivalolactone or ε-caprolactone. Useful polyols include the abovementioned polyfunctional alcohols, preferably neopentylglycol, trimethylolpropane, trimethylolethane, pentaerythritol, dimethylolpropionic acid or dimethylolbutyric acid.

Preferred examples of such polyesterols are polyesterols of the formula (IIIa–c),

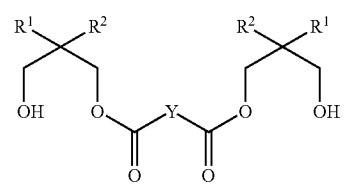

(IIIa)

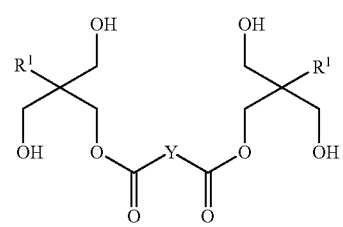

(IIIb)

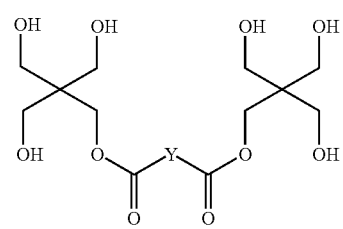

(IIIc)

where
$R^1$ and $R^2$ are each as defined above, and
Y is a straight-chain or branched, optionally substituted alkylene group of 2 to 20 carbon atoms or an optionally substituted cycloalkylene or arylene group of 6 to 12 carbon atoms or a single bond.

Examples of Y are a single bond, methylene, 1,2-ethylene, 1,3-propylene, 1,4-butylene, 1,6-hexylene, 1,7-heptylene, 1,8-octylene, cis-1,2-ethenylene, trans-11,2-ethenylene, 1,2-, 1,3- or 1,4-phenylene, 1,2-cyclohex-1-enylene, 1,2-, 1,3- or 1,4-cyclohexylene, 4-carboxy-1,2-phenylene, 2-carboxy-1,4-phenylene or 1-carboxy-2,4-phenylene.

Preferred Y groups are 1,2-ethylene, 1,4-butylene and 1,2-, 1,3- or 1,4-phenylene.

It will be appreciated that the method of making generally produces mixtures which may additionally contain lower and higher oligomers.

In a further preferred embodiment, reaction mixtures of at least partially hydrolyzed polyesterols are used as polyalcohols A for producing the ester F.

To this end, the polyesterols described above, for example, are at least partially hydrolyzed with a suitable base and subsequently and if appropriate after removal of the basic constituents remaining in the reaction mixture esterified with the carboxylic acid B.

Useful bases include for example NaOH, KOH, Ca(OH)$_2$, milk of lime, Na$_2$CO$_3$ or K$_2$CO$_3$, for example as solid, solution or suspension, preferably in the form of a 10–50% by weight solution and more preferably in the form of a 20–40% by weight aqueous solution.

The extent to which the ester groups in the polyesterol are hydrolyzed, ie cleaved, is for example at least 10% (based on the ester groups in the starting compound), preferably at least 25%, more preferably at least 50%, even more preferably at least 75% and most preferably at least 90%.

When basic constituents, for example the basic salt of the carboxylic acid, are to be removed from the reaction mixture, this may be effected for example via ion exchangers, for example acidic or strongly acidic ion exchangers.

The reaction mixture is subsequently acidified and esterified with the carboxylic acid B as described.

Polyester (meth)acrylates may be prepared in multiple stages or else in a single stage, as described for example in EP-A 279 303, from (meth)acrylic acid, polycarboxylic acid and polyol.

Useful polyalcohols further include alkoxylated polyols and polyesterols which are obtainable by reaction of a polyol or polyesterol with at least one alkylene oxide.

The present invention further provides reaction mixtures of compounds of the formula VII $$R^8-(O(CH(R^{10})CH(R^{10})O)_y-C(=O)-R^9)_x \quad (VII),$$

where $R^8$ is a polyvalent straight-chain or branched $C_2$–$C_{10}$-alkyl radical, $R^9$ is independently in each occurrence a straight-chain or branched $C_2$–$C_{10}$-alkenyl radical, $R^{10}$ is independently in each occurrence hydrogen or methyl, x is independently in each occurrence a positive integer of 2 or greater, and y is independently in each occurrence a number from 3 to 8 for x=2 and a number from 2 to 7 for x=3 or greater.

The underlying alcohol to be esterified has the formula VIIa $$R^8-(O(CH(R^{10})CH(R^{10})O)_y-H)_x \quad (VIIa),$$

where $R^8$, $R^{10}$, x and y are each as defined above.

The compounds of the formula (VII) are generally $C_2$–$C_{10}$ polyhydric alcohols VIIa which have been alkoxylated with between 2 and 8 alkylene oxide units per hydroxyl group and wherein the terminal hydroxyl group of each alkylene oxide chain is esterified with a $C_2$–$C_{10}$ unsaturated carboxylic acid or ester. Preferably the starting alcohol is a $C_3$–$C_6$ polyhydric alcohol which preferably has from 2 to 4 hydroxyl groups. More preferably the starting alcohol is trimethylolpropane, glycerol, pentaerythritol, 1,3-propanediol, propylene glycol, 1,4-butanediol or butylene glycol. Most preference as starting alcohols is given to trimethylolpropane, glycerol and pentaerythritol.

Useful alkylene oxides include for example ethylene oxide, propylene oxide, iso-butylene oxide, vinyloxirane and/or styrene oxide.

The alkylene oxide chain may preferably be made up of ethylene oxide, propylene oxide and/or butylene oxide units. Such a chain can be made up of one species of an alkylene oxide or of a mixture of alkylene oxides. When a mixture is used, the different alkylene oxide units may be arranged in a random pattern or as a block or blocks of each species. Preferably the alkylene oxide is ethylene oxide, propylene oxide or a mixture thereof, more preferably it is ethylene oxide or propylene oxide and most preferably it is ethylene oxide. It is thus preferable for one $R^{10}$ radical per alkylene oxide unit to be hydrogen while the other is methyl or hydrogen and is more preferable for both the $R^{10}$ radicals to be hydrogen.

The preferred number of alkylene oxide units in each chain is dependent upon the number of chains.

The esterifying agent is a $C_2$–$C_{10}$ straight- or branched-chain ethylenically unsaturated carboxylic acid or ester, preferably a $C_2$–$C_4$ and more preferably a $C_2$–$C_3$ ethylenically unsaturated carboxylic acid, even more preferably acrylic acid, methacrylic acid or ester and most preferably acrylic acid.

The compounds of the formula VII are frequently present as a mixture of compounds described by this formula and by-products resulting from the preparation process.

Particular preference among these compounds VII is given to those compounds—hereinafter referred to as compounds VIIb—which have been reacted with up to six, more preferably up to four and most preferably four ethylene oxide units per hydroxyl group. These compounds VIIb possess enhanced hydrolytic stability.

Preference is similarly given to compounds VII—hereinafter referred to as compounds VIIc—which for x=2 have been reacted with more than eight, more preferably more than ten, even more preferably more than twelve and especially not less than 15 or for x=3 or greater with more than seven, more preferably more than nine, even more preferably more than twelve and most preferably not less than 15 ethylene oxide units per hydroxyl group, since these compounds VIIc generally possess enhanced solubility in water.

Also conceivable are compounds VII where y is 0, 1 or 2 for x=2 and 0 or 0.1 for x=3.

Of particular advantage are mixtures of the compounds VIIb and VIIc, for example mixtures having a VIIb:VIIc weight ratio in the range from 10:90 to 90:10, preferably in the range from 20:80 to 80:20, more preferably in the range from 30:70 to 70:30 and most preferably in the range from 40:60 to 60:40.

Preferred examples of such alkoxylated polyols are the alkoxylation products (IIa), (IIb) or (IIc) of polyols of the formula (I),

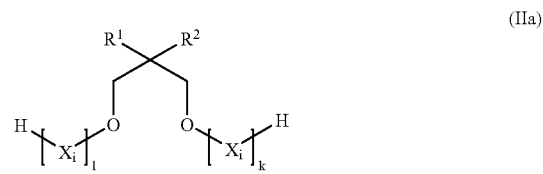

(IIa)

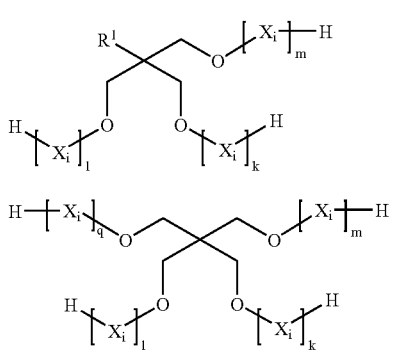

where
R[1] and R[2] are each as defined above,
k, l, m and q are independently an integer from 1 to 10, preferably from 1 to 5, more preferably from 3 to 5 and most preferably 4, and
each $X_i$ for i=1 to k, 1 to l, 1 to m and 1 to q can be independently selected from the group consisting of —CH$_2$—CH$_2$—O—, —CH$_2$—CH(CH$_3$)—O—, —CH(CH$_3$)—CH$_2$—O—, —CH$_2$—C(CH$_3$)$_2$—O—, —C(CH$_3$)$_2$—CH$_2$—O—, —CH$_2$—CHVin—O—, —CHVin—CH$_2$—O—, —CH$_2$—CHPh—O— and —CHPh—CH$_2$—O—, preferably from the group consisting of —CH$_2$—CH$_2$—O—, —CH$_2$—CH(CH$_3$)—O— and —CH(CH$_3$)—CH$_2$—O—, and more preferably —CH$_2$—CH$_2$—O—, where Ph is phenyl and Vin is vinyl.

The compounds in question are preferably from singly to quintuply, more preferably from triply to quintuply and most preferably quadruply ethoxylated, propoxylated or mixedly ethoxylated and propoxylated and especially exclusively ethoxylated neopentylglycol, trimethylolpropane, trimethylolethane or pentaerythritol.

Particular preference among these is given to such polyhydric alcohols of the formula (IIb).

Preference is similarly given to a from singly to 20-tuply, preferably from singly to 10-tuply, more preferably from doubly to 10-tuply, even more preferably from doubly to quintuply, especially from triply to quintuply and specifically from triply to quadruply alkoxylated and preferably ethoxylated, propoxylated or mixedly ethoxylated/propoxylated and more preferably ethoxylated glycerol (here exceptionally reckoned in moles of alkoxy groups per mole of glycerol).

Indicated degrees of alkoxylation are each based on the average degree of alkoxylation.

The number average molecular weight $M_n$ of the alkoxylated polyols is preferably not more than 1000 g/mol, more preferably not more than 800 g/mol and most preferably not more than 550 g/mol.

The statements concerning the number average and weight average molecular weights $M_n$ and $M_w$ are here based on gel permeation chromatography measurements using polystyrene as a standard and tetrahydrofuran as a mobile phase. The method is described in Analytiker Taschenbuch Vol. 4, pages 433 to 442, Berlin 1984.

Examples of alkoxylated sugar alcohols are compounds obtainable from sugar alcohols, for example from the above-recited sugar alcohols, by alkoxylation, for example with the above-recited alkylene oxides, preferably with ethylene oxide and/or propylene oxide and most preferably with ethylene oxide.

Examples thereof are
- the recited tetrols which have been alkoxylated on average with 2–30, preferably 2–20, more preferably 3–10 and especially 3, 4, 5, 6, 7 or 8 alkylene oxide units per mole of sugar alcohol,
- the recited pentols which have been alkoxylated on average with 3–35, preferably 3–28, more preferably 4–20 and especially 4, 5, 6, 7, 8, 9 or 10 alkylene oxide units per mole of sugar alcohol,
- higher sugar alcohols which have been alkoxylated on average with 4–50, preferably 6–40, more preferably 7–30, even more preferably 8–20 and most preferably 10–15 alkylene oxide units per mole of sugar alcohol.

Preferred alkoxylated sugar alcohols are alkoxylated sugar alcohols wherein at least one hydroxyl group of the sugar alcohol has not been alkoxylated.

Preferred examples of alkoxylated polyesterols are alkoxylated polyesterols of the formula (IVa–c),

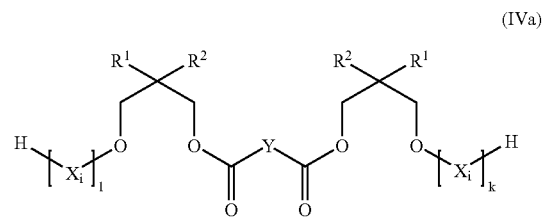

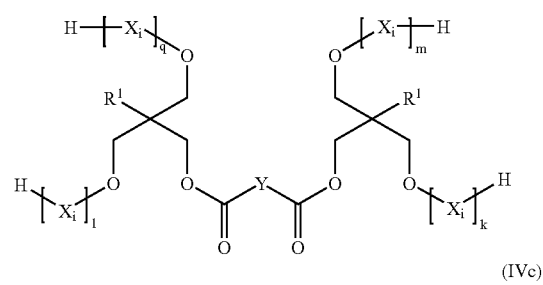

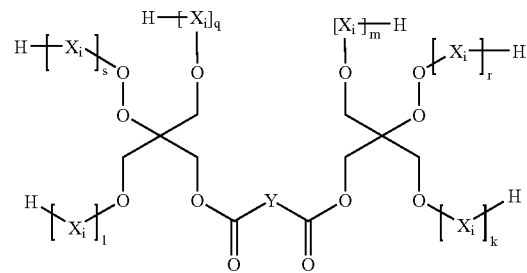

where
R[1], R[2] and Y are each as defined above,
k, l, m, q, r and s are independently an integer from 1 to 30, preferably from 1 to 20, more preferably from 1 to 10 and most preferably from 1 to 5, and
each $X_i$ for i=1 to k, 1 to l, 1 to m, 1 to q, 1 to r and 1 to s can be independently selected from the group consisting of —CH$_2$—CH$_2$—O—, —CH$_2$—CH(CH$_3$)—O—, —CH(CH$_3$)—CH$_2$O—, —CH$_2$—C(CH$_3$)$_2$O—, —C(CH$_3$)$_2$—CH$_2$O —, —CH$_2$—CHVin—O—, —CHVin—CH$_2$—O—, —CH$_2$—CHPh—O— and —CHPh—CH$_2$—O—, preferably from the group consisting of —CH$_2$—CH$_2$—O—, —CH$_2$—CH(CH$_3$)—O— and —CH(CH$_3$)—CH$_2$—O—, and more preferably —CH$_2$—CH$_2$—O—, where Ph is phenyl and Vin is vinyl.

The compounds in question are preferably nonalkoxylated or from singly to 10-tuply and more preferably from doubly to quintuply ethoxylated, propoxylated or mixedly ethoxylated and propoxylated esterification products of neopentylglycol, trimethylolpropane, trimethylolethane or pentaerythritol with adipic acid, phthalic acid, terephthalic acid or isophthalic acid.

The reaction of alcohols with an alkylene oxide is known per se to one skilled in the art. Possible procedures may be found in Houben-Weyl, Methoden der Organischen Chemie, 4th edition, 1979, Thieme Verlag Stuttgart, ed. Heinz Kropf, volume 6/1a, Part 1, pages 373 to 385.

When mixedly alkoxylated alcohols are used, the different alkoxy groups present therein may be portioned in a molar ratio to each other of for example 0.05–20:1, preferably 0.1–10:1 and more preferably 0.2–5:1.

The viscosity of the polyalcohols which can be used according to the present invention is not subject to any particular requirements bar that they should be readily pumpable to about 80° C., preferably they should have a viscosity below 1000 mPas, preferably below 800 mPas and most preferably below 500 mPas.

When the polyalcohols used in the esterification have three or more hydroxyl groups, it can be sensible for their use according to the present invention, as radical crosslinkers, for them to be merely partially esterified. In other words, in the case of an n-hydric polyalcohol only at least two of the n hydroxyl groups are esterified with the carboxylic acid B.

For n=3 the degree of esterification is at least 2, for n=4 it is at least 2, preferably at least 2.5 and more preferably at least 3, for n=5 or greater it is at least 2, preferably at least 3 and more preferably at least 4.

In such a case, the target stoichiometric excess of carboxylic acid B is dependent on the target degree of esterification and is thus for example 2/n times the above-indicated molar excesses. It will be appreciated that the esterification can also be discontinued, for example by cooling or dilution, once the desired degree of esterification is reached.

Useful ethylenically unsaturated carboxylic acids B for the present invention include compounds having at least one carboxyl group (—COOH), preferably one, and at least one and preferably one ethylenically unsaturated group.

Useful carboxylic acids for the present invention can be aliphatic, cycloaliphatic or aromatic, preferably aliphatic or cycloaliphatic and most preferably aliphatic, straight-chain or branched and optionally substituted by functional groups.

The carboxylic acids generally have from three to ten carbon atoms, preferably from three to five carbon atoms and more preferably from three to four carbon atoms.

Examples of ethylenically unsaturated carboxylic acids B are acrylic acid, methacrylic acid, ethacrylic acid, maleic acid, maleic anhydride, fumaric acid, itaconic acid, citraconic acid, mesaconic acid, vinylacetic acid, allylacetic acid and crotonic acid.

Preferred carboxylic acids B are α,β-unsaturated carboxylic acids.

Particular preference is given to methacrylic acid and acrylic acid, herein referred to as (meth)acrylic acid, and acrylic acid is most preferred.

Useful esterification catalysts C for the present invention are sulfuric acid, aryl or alkyl sulfonic acids or mixtures thereof. Examples of aryl sulfonic acids are benzenesulfonic acid, para-toluenesulfonic acid and dodecylbenzenesulfonic acid, and examples of alkyl sulfonic acids are methanesulfonic acid, ethanesulfonic acid and trifluoromethanesulfonic acid. Similarly, strongly acidic ion exchangers or zeolites are useful as esterification catalysts. Preference is given to sulfuric acid and ion exchangers.

Useful polymerization inhibitors D for the present invention include for example phenols such as alkylphenols, for example, o-, m- or p-cresol (methylphenol), 2-tert-butyl-4-methylphenol, 6-tert-butyl-2,4-dimethylphenol, 2,6-di-tert-butyl-4-methylphenol, 2-tert-butylphenol, 4-tert-butylphenol, 2,4-di-tert-butylphenol, 2-methyl-4-tert-butylphenol, 4-tert-butyl-2,6-dimethylphenol, or 2,2'-methylenebis(6-tert-butyl-4-methylphenol), 4,4'-oxydiphenyl, 3,4-methylenedioxydiphenol (sesamol), 3,4-dimethylphenol, hydroquinone, pyrocatechol (1,2-dihydroxybenzene), 2-(1'-methylcyclohex-1'-yl)-4,6-dimethylphenol, 2- or 4-(1'-phenyleth-1'-yl)phenol, 2-tert-butyl-6-methylphenol, 2,4,6-tris-tert-butylphenol, 2,6-di-tert-butylphenol, 2,4-di-tert-butylphenol, 4-tert-butylphenol, nonylphenol [11066-49-2], octylphenol [140-66-9], 2,6-dimethylphenol, bisphenol A, bisphenol F, bisphenol B, bisphenol C, bisphenol S, 3,3',5,5'-tetrabromobisphenol A, 2,6-di-tert-butyl-p-cresol, Koresin® from BASF AG, methyl 3,5-di-tert-butyl-4-hydroxybenzoate, 4-tert-butylpyrocatechol, 2-hydroxybenzyl alcohol, 2-methoxy-4-methylphenol, 2,3,6-trimethylphenol, 2,4,5-trimethylphenol, 2,4,6-trimethylphenol, 2-isopropylphenol, 4-isopropylphenol, 6-isopropyl-m-cresol, n-octadecyl β-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)-benzene, 1,3,5-tris(3,5-di-tert-butyl-4-hydroxybenzyl) isocyanurate, 1,3,5-tris(3,5-di-tert-butyl-4-hydroxyphenyl) propionyloxyethyl isocyanurate, 1,3,5-tris(2,6-dimethyl-3-hydroxy-4-tert-butylbenzyl) isocyanurate or pentaerythritol tetrakis [β-(3,5-di-tert-butyl-4-hydroxyphenyl)propionate], 2,6-di-tert-butyl-4-dimethylaminomethylphenol, 6-sec-butyl-2,4-dinitrophenol, Irganox® 565, 1141, 1192, 1222 and 1425 from Ciba Spezialitatenchemie, octadecyl 3-(3',5'-di-tert-butyl-4'-hydroxyphenyl)propionate, hexadecyl 3-(3',5'-di-tert-butyl-4'-hydroxyphenyl)propionate, octyl 3-(3',5'-di-tert-butyl-4'-hydroxyphenyl)propionate, 3-thia-1,5-pentanediol bis[(3',5'-di-tert-butyl-4'-hydroxyphenyl) propionate], 4,8-dioxa-1,11-undecanediol bis[(3',5'-di-tert-butyl-4'-hydroxyphenyl)propionate], 4,8-dioxa-1,11-undecanediol bis[(3'-tert-butyl-4'-hydroxy-5'-methylphenyl) propionate], 1,9-nonanediol bis[(3',5'-di-tert-butyl-4'-hydroxyphenyl)propionate], 1,7-heptanediamine bis[3-(3',5'-di-tert-butyl-4'-hydroxyphenyl)propionamide], 1,1-methanediamine bis[3-(3',5'-di-tert-butyl-4'-hydroxyphenyl) propionamide], 3-(3',5'-di-tert-butyl-4'-hydroxyphenyl) propionic acid-hydrazide, 3-(3',5'-di-methyl-4'-hydroxyphenyl)propionic acid hydrazide, bis(3-tert-butyl-5-ethyl-2-hydroxyphen-1-yl)methane, bis(3,5-di-tert-butyl-4-hydroxyphen-1-yl)methane, bis[3-(1'-methylcyclohex-1'-yl)-5-methyl-2-hydroxyphen-1-yl]methane, bis(3-tert-butyl-2-hydroxy-5-methylphen-1-yl)methane, 1,1-bis(5-tert-butyl-4-hydroxy-2-methylphen-1-yl)ethane, bis(5-tert-butyl-4-hydroxy-2-methylphen-1-yl) sulfide, bis(3-tert-butyl-2-hydroxy-5-methylphen-1-yl) sulfide, 1,1-bis(3,4-dimethyl-2-hydroxyphen-1-yl)-2-methylpropane, 1,1-bis(5-tert-butyl-3-methyl-2-hydroxyphen-1-yl)butane, 1,3,5-tris [1'-(3",5"-di-tert-butyl-4"-hydroxyphen-1"-yl)meth-1'-yl]-2,4,6-trimethylbenzene, 1,1,4-tris(5'-tert-butyl-4'-hydroxy-2'-methylphen-1'-yl)butane, aminophenols, for example para-aminophenol, nitrosophenols, for example paranitrosophenol, p-nitroso-o-cresol, alkoxyphenols, for example 2-methoxyphenol (guajacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol, 3,5-di-tert-butyl-4-hydroxyanisole, 3-hydroxy-4-methoxybenzyl alcohol, 2,5-dimethoxy-4-hydroxybenzyl alcohol (syringa alcohol), 4-hydroxy-3-methoxybenzaldehyde (vanillin), 4-hydroxy-3-ethoxybenzaldehyde (ethylvanillin), 3-hydroxy-4-methoxybenzaldehyde (isovanillin), 1-(4-hydroxy-3-methoxyphenyl)ethanone (acetovanillone), eugenol, dihydroeugenol, isoeugenol, tocopherols, for example α-, β-, γ-, δ- and ε-tocopherol, tocol, α-tocopherolhydroquinone, and also 2,3-dihydro-2,2-dimethyl-7-hydroxybenzofuran (2,2-dimethyl-7-hydroxycoumaran), quinones and hydroquinones such as hydroquinone or hydroquinone monomethyl ether, 2,5-di-tert-butylhydroquinone, 2-methyl-p-hydroquinone, 2,3-dimethylhydroquinone, trimethylhydroquinone, 4-methylpyrocatechol, tert-butylhydroquinone, 3-methylpyrocatechol, benzoquinone, 2-methyl-p-hydroquinone, 2,3-dimethylhydroquinone, trimethylhydroquinone, 3-methylpyrocatechol, 4-methylpyrocatechol, tert-butylhydroquinone, 4-ethoxyphenol, 4-butoxyphenol, hydroquinone monobenzyl ether, p-phenoxyphenol, 2-methylhydroquinone, 2,5-di-tert-butylhydroquinone, tetramethyl-p-benzoquinone, diethyl 1,4-cyclohexanedion-2,5-dicarboxylate, phenyl-p-benzoquinone, 2,5-dimethyl-3-benzyl-p-benzoquinone, 2-isopropyl-5-methyl-p-benzoquinone (thymoquinone), 2,6-diisopropyl-p-benzoquinone, 2,5-dimethyl-3-hydroxy-p-benzoquinone, 2,5-dihydroxy-p-benzoquinone, embelin, tetrahydroxy-p-benzoquinone, 2,5-dimethoxy-1,4-benzoquinone, 2-amino-5-methyl-p-benzoquinone, 2,5-bisphenylamino-1,4-benzoquinone, 5,8-dihydroxy-1,4-naphthoquinone, 2-anilino-1,4-naphthoquinone, anthraquinone, N,N-dimethylindoaniline, N,N-diphenyl-p-benzoquinonediimine, 1,4-benzoquinone dioxime, coerulignone, 3,3'-di-tert-butyl-5,5'-dimethyldiphenoquinone, p-rosolic acid (aurine), 2,6-di-tert-butyl-4-benzylidenebenzoquinone, 2,5-di-tert-amylhydroquinone, nitroxide free radicals such as 4-hydroxy-2,2,6,6-tetramethylpiperidinyloxy free radical, 4-oxo-2,2,6,6-tetramethylpiperidinyloxy free radical, 4-acetoxy-2,2,6,6-tetramethylpiperidinyloxy free radical, 2,2,6,6-tetramethylpiperidinyloxy free radical, 4,4',4"-tris(2,2,6,6-tetramethylpiperidinyloxy) phosphite, 3-oxo-2,2,5,5-tetramethylpyrrolidinyloxy free radical, 1-oxyl-2,2,6,6-tetramethyl-4-methoxypiperidine, 1-oxyl-2,2,6,6-tetramethyl-4-trimethylsilyloxypiperidine, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl (4-tert-butyl)benzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethyl-4-piperidinyl) 1,10-decanedioate, bis(1-oxyl-2,2,6,6-tetramethyl-4-piperidinyl) n-butylmalonate, bis(1-oxyl-2,2,6,6-tetramethyl-4-piperidinyl) phthalate, bis(1-oxyl-2,2,6,6-tetramethyl-4-piperidinyl) isophthalate, bis(1-oxyl-2,2,6,6-tetramethyl-4-piperidinyl) terephthalate, bis(1-oxyl-2,2,6,6-tetramethyl-4-piperidinyl) hexahydroterephthalate, N,N'-bis(1-oxyl-2,2,6,6-tetramethyl-4-piperidinyl)adipamide, N-(1-oxyl-2,2,6,6-tetramethyl-4-piperidinyl)caprolactam, N-(1-oxyl-2,2,6,6-tetramethyl-4-piperidinyl)dodecylsuccinimide, 2,4,6-tris [N-butyl-N-(1-oxyl-2,2,6,6-tetramethyl-4-piperidinyl]-triazine, N,N'-bis(1-oxyl-2,2,6,6-tetramethyl-4-piperidinyl)-N,N'bisformyl-1,6-diaminohexane, 4,4'-ethylenebis(1-oxyl-2,2,6,6-tetramethyl-3-piperazinone), aromatic amines such as phenylenediamines, N,N-diphenylamine, N-nitrosodiphenylamine, nitrosodiethylaniline, N,N'-dialkyl-para-phenylenediamine, wherein the alkyl radicals can be the same or different and may each independently contain from 1 to 4 carbon atoms and be straight-chain or branched, for example N,N'-di-iso-butyl-p-phenylenediamine, N,N'-di-iso-propyl-p-phenylenediamine, Irganox 5057 from Ciba Spezialitätenchemie, N,N'-di-iso-butyl-p-phenylenediamine, N,N'-di-iso-propyl-p-phenylenediamine, p-phenylenediamine, N-phenyl-p-phenylenediamine, N,N'-diphenyl-p-phenylenediamine, N-isopropyl-N-phenyl-p-phenylenediamine, N,N'-di-sec-butyl-p-phenylenediamine (Kerobit® BPD from BASF AG), N-phenyl-N'-isopropyl-p-phenylenediamine (Vulkanox® 4010 from Bayer AG), N-(1,3-dimethylbutyl)-N'-phenyl-p-phenylenediamine, N-phenyl-2-naphthylamine, imoinodibenzyl, N,N'-diphenylbenzidine, N-phenyltetraaniline, acridone, 3-hydroxydiphenylamine, 4-hydroxydiphenylamine, hydroxylamines such as N,N-diethylhydroxylamine, urea derivatives such as urea or thiourea, phosphorus compounds, such as triphenylphosphine, triphenyl phosphite, hypophosphorous acid or triethyl phosphite, sulfur compounds such as diphenyl sulfide, phenothiazine or metal salts, for example copper chloride, copper dithiocarbamate, copper sulfate, copper salicylate, copper acetate, manganese chloride, manganese dithiocarbamate, manganese sulfate, manganese salicylate, manganese acetate, cerium chloride, cerium dithiocarbamate, cerium sulfate, cerium salicylate, cerium acetate, nickel chloride, nickel dithiocarbamate, nickel sulfate, nickel salicylate, nickel acetate, chromium chloride, chromium dithiocarbamate, chromium sulfate, chromium salicylate, chromium acetate or mixtures thereof. Preference is given to the phenols and quinones mentioned, particular preference is given to hydroquinone, hydroquinone monomethyl ether, 2-tert-butyl-4-methylphenol, 6-tert-butyl-2,4-dimethylphenol, 2,6-di-tert-butyl-4-methylphenol, 2,4-di-tert-butylphenol, triphenyl phosphite, hypophosphorous acid, $CuCl_2$ and guajacol, and very particular preference is given to hydroquinone and hydroquinone monomethyl ether.

Particular preference is given to hydroquinone monomethyl ether, hydroquinone and alkylphenols, optionally in combination with triphenyl phosphite and/or hypophosphorous acid.

Stabilization may be further supported by the presence of an oxygen-containing gas, preferably air or a mixture of air and nitrogen (lean air).

Among the recited stabilizers, preference is given to those which are aerobic, ie those which require the presence of oxygen to fully develop their inhibiting effect.

Useful solvents E for the present invention are particularly solvents which are suitable for azeotropic removal of the water of reaction, if desired, in particular aliphatic, cycloaliphatic and aromatic hydrocarbons or mixtures thereof.

Preference is given to n-pentane, n-hexane, n-heptane, cyclohexane, methylcyclohexane, benzene, toluene or xylene. Particular preference is given to cyclohexane, methylcyclohexane and toluene.

The esterification may be carried out by conventional preparation and/or workup processes for polyhydric alcohols, for example the processes mentioned at the beginning or the processes described in DE-A 199 41 136, DE-A 38 43 843, DE-A 38 43 854, DE-A 199 37 911, DE-A 199 29 258, EP-A 331 845, EP 554 651 or U.S. Pat. No. 4,187,383.

In general, the esterification may be carried out as follows:

The esterification apparatus comprises a stirrer reactor, preferably a reactor with circulatory evaporator and an added distillation unit with condenser and phase separation vessel.

The reactor may be for example a reactor with jacketed heating and/or internal heating coils. Preference is given to using a reactor having an external heat exchanger and natural or forced circulation, ie through use of a pump, more preferably natural circulation where circulation is accomplished without mechanical aids.

It will be appreciated that the reaction can also be carried out in a plurality of reaction zones, for example a reactor battery of two to four and preferably two or three reactors.

Suitable circulatory evaporators are known to one skilled in the art and are described for example in R. Billet, Verdampfertechnik, HTB-Verlag, Bibliographisches Institut Mannheim, 1965, 53. Examples of circulatory evaporators are tube-bundle heat exchangers, plate-type heat exchangers, etc.

It will be appreciated that the circulatory system may also include a plurality of heat exchangers.

The distillation unit is of conventional design. It may be a simple distillation unit which if appropriate is equipped with a splash guard or it may be a rectification column. Suitable column internals include in principle all common internals, for example trays, structured packings and/or dumped packings. Preferred trays include bubble trays, sieve trays, valve trays, Thormann trays and/or dual-flow trays, while preferred dumped packings are those of rings, coils, saddles or braids.

In general, from 5 to 20 theoretic plates are sufficient.

The condenser and the separation vessel are of traditional design.

The carboxylic acid B and the polyalcohol A are generally used in the esterification a) in a molar excess as indicated above, based on the hydroxyl groups of the alcohol. The excess used can be up to about 1000:1, if desired.

Useful esterification catalysts C include those recited above.

They are generally used in an amount of 0.1–5% by weight, based on the esterification mixture, preferably 0.5–5%, more preferably 1–4% and most preferably 2–4% by weight.

If necessary, the esterification catalyst can be removed from the reaction mixture with the aid of an ion exchanger. The ion exchanger can be added directly to the reaction mixture and then subsequently filtered off, or the reaction mixture can be passed through an ion exchanger bed.

Preferably, the esterification catalyst is left in the reaction mixture. However, where the catalyst is an ion exchanger, the ion exchanger is preferably removed, for example by filtration.

Stabilization may be further supported by the presence of an oxygen-containing gas, preferably air or a mixture of air and nitrogen (lean air).

This oxygen-containing gas is preferably metered into the bottom region of a column and/or into a circulatory evaporator and/or passed through and/or over the reaction mixture.

The polymerization inhibitor (mixture) D (as indicated above) is used in a total amount of 0.01–1% by weight, based on the esterification mixture, preferably 0.02–0.8% and more preferably 0.05–0.5% by weight.

The polymerization inhibitor (mixture) D may be used for example as an aqueous solution or as a solution in a reactant or product.

b) The water of reaction formed in the course of the reaction can be distilled off during or after the esterification a), in which case this operation can be augmented by a solvent which forms an azeotrope with water.

Useful solvents E for azeotropic removal of the water of reaction, if desired, include the compounds recited above.

The esterification is preferably carried out in the presence of a solvent.

The amount of solvent used is 10–200% by weight, preferably 20–100% by weight and more preferably from 30% to 100% by weight, based on the sum total of polyalcohol and carboxylic acid B.

However, an operation without entrainer is also conceivable, as described for example in DE-A1 38 43 854, column 2 line 18 to column 4 line 45, but in contradistinction to the cited reference with the abovementioned stabilizers.

When the water in the reaction mixture is not removed via an azeotrope-forming solvent, it may be removed by stripping with an inert gas, preferably an oxygen-containing gas and more preferably air or lean air as described for example in DE-A 38 43 843.

The reaction temperature for the esterification a) is generally in the range from 40 to 160° C., preferably in the range from 60 to 140° C. and more preferably in the range from 80 to 120° C. The temperature may remain constant or rise in the course of the reaction and preferably it is raised in the course of the reaction. In this case, the final temperature of the esterification is 5–30° C. higher than the initial temperature. The temperature of the esterification can be determined and controlled by varying the solvent concentration in the reaction mixture, as described in DE-A 199 41 136 and the German application under file reference 100 63 175.4.

When a solvent is used, it can be distilled out of the reaction mixture through the distillation unit added on top of the reactor.

The distillate may selectively be removed or, after condensation, fed into a phase separation apparatus. The aqueous phase thus obtained is generally removed from the system, while the organic phase can be fed as reflux into the distillation unit and/or passed directly into the reaction zone and/or fed into a circulatory evaporator as described in the German patent application under file reference 100 63 175.4.

When used as reflux, the organic phase can be used as described in DE-A 199 41 136 for controlling the temperature in the esterification.

The esterification a) can be carried out with no pressure, at superatmospheric or reduced pressure and is preferably carried out at atmospheric pressure.

The reaction time is generally in the range from 2 to 20 hours, preferably in the range from 4 to 15 hours and more preferably in the range from 7 to 12 hours.

The order in which the individual reaction components are added is not essential to the present invention. All components can be introduced as a mixed initial charge and subsequently heated, or one or more components may be omitted from or only partly included in the initial charge and added only after the initial charge has been heated up.

The carboxylic acid B which can be used is not restricted in its composition and in the case of crude (meth)acrylic acid may comprise for example the following components:

| | |
|---|---|
| (Meth)acrylic acid | 90–99.9% by weight |
| Acetic acid | 0.05–3% by weight |

-continued

| | |
|---|---|
| Propionic acid | 0.01–1% by weight |
| Diacrylic acid | 0.01–5% by weight |
| Water | 0.05–5% by weight |
| Carbonylics | 0.01–0.3% by weight |
| Inhibitors | 0.01–0.1% by weight |
| Maleic acid or anhydride | 0.001–0.5% by weight |

The crude (meth)acrylic acid used is generally stabilized with 200–600 ppm of phenothiazine or other stabilizers in amounts which permit comparable stabilization. Carbonylics here refers for example to acetone and lower aldehydes, for example formaldehyde, acetaldehyde, crotonaldehyde, acrolein, 2-furfural, 3-furfural and benzaldehyde.

Crude (meth)acrylic acid here refers to the (meth)acrylic acid mixture which is obtained after absorption of the reaction gases of the propane/propene/acrolein or isobutane/isobutene/methacrolein oxidation in an absorbent and subsequent removal of the absorbent, or which is obtained by fractional condensation of the reaction gases.

It is obviously also possible to use pure (meth)acrylic acid, for example of the following purity:

| | |
|---|---|
| (Meth)acrylic acid | 99.7–99.99% by weight |
| Acetic acid | 50–1000 weight ppm |
| Propionic acid | 10–500 weight ppm |
| Diacrylic acid | 10–500 weight ppm |
| Water | 50–1000 weight ppm |
| Carbonylics | 1–500 weight ppm |
| Inhibitors | 1–300 weight ppm |
| Maleic acid or anhydride | 1–200 weight ppm |

The pure (meth)acrylic acid used is generally stabilized with 100–300 ppm of hydroquinone monomethyl ether or other storage stabilizers in amounts which permit comparable stabilization.

Pure or prepurified (meth)acrylic acid generally refers to (meth)acrylic acid whose purity is at least 99.5% by weight and which is substantially free of aldehydic, other carbonylic and high-boiling components.

The aqueous phase, distilled off during the esterification, of the condensate removed via the added column (if present) may generally contain 0.1–10% by weight of carboxylic acid B, for example (meth)acrylic acid, and is separated off and removed from the system. The carboxylic acid, for example (meth)acrylic acid, it contains may preferably be extracted with an extractant, preferably with any solvent used in the esterification, for example with cyclohexane, at from 10 to 40° C. and a ratio of 1:5–30 and preferably 1:10–20 for aqueous phase to extractant, and returned into the esterification.

Circulation may be further supported by passing an inert gas, preferably an oxygen-containing gas, more preferably air or a mixture of air and nitrogen (lean air) into the circulation or through or over the reaction mixture, for example at rates of 0.1–1, preferably 0.2–0.8 and more preferably 0.3–0.7 $m^3/m^3h$, based on the volume of the reaction mixture.

The course of the esterification a) can be monitored by monitoring the amount of water carried out and/or the decrease in the carboxylic acid concentration in the reactor.

The reaction can be ended for example as soon as 90%, preferably at least 95% and more preferably at least 98% of the theoretically expected amount of water has been carried out by the solvent.

The end of the reaction can be detected for example from the fact that substantially no further water of reaction is removed via the entrainer. When carboxylic acid B is carried out together with the water of reaction, its fraction is determinable for example by backtitrating an aliquot of the aqueous phase.

The removal of the water of reaction can be dispensed with for example when the carboxylic acid B is used in a high stoichiometric excess, for example of at least 1.5:1, preferably at least 2.5:1 and most preferably at least 5:1. In this case, a substantial portion of the amount of water formed will remain in the reaction mixture. Merely that fraction of water is removed from the reaction mixture during or after the reaction which is determined by the volatility at the employed temperature and beyond that no measures are carried out to remove the resulting water of reaction. For instance, at least 10% by weight of the resulting water of reaction can remain in the reaction mixture, preferably at least 20% by weight, more preferably at least 30% by weight, even more preferably at least 40% by weight and most preferably at least 50% by weight.

c) After the end of the esterification the reaction mixture can be conventionally cooled to 10–30° C. and if necessary by addition of a solvent which may be the same as any solvent used for azeotropic removal of water or a different solvent adjusted to any desired target ester concentration.

In a further embodiment, the reaction can stopped with a suitable diluent G and diluted to a concentration of for example 10–90% by weight, preferably 20–80%, more preferably 20–60%, even more preferably 30–50% and most preferably about 40%, for example in order to reduce the viscosity.

What is important is that a substantially homogeneous solution forms after dilution.

This is preferably accomplished only relatively shortly before use in the production of the hydrogel, for example not more than 24 hours before, preferably not more than 20 hours before, more preferably not more than 12 hours before, even more preferably not more than 6 hours before and most preferably not more than 3 hours before.

The diluent G is selected from the group consisting of water, a mixture of water with one or more organic solvents which are soluble in water in any proportion and a mixture of water with one or more monohydric or polyhydric alcohols, for example methanol and glycerol. The alcohols preferably bear 1, 2 or 3 hydroxyl groups and preferably have from 1 to 10 and especially up to 4 carbon atoms. Preference is given to primary and secondary alcohols.

Preferred alcohols are methanol, ethanol, isopropanol, ethylene glycol, 1,2-propanediol and 1,3-propanediol.

d) If necessary, the reaction mixture may be decolorized, for example by treatment with active carbon or metal oxides, for example alumina, silica, magnesium oxide, zirconium oxide, boron oxide or mixtures thereof, in amounts for example of 0.1–50% by weight, preferably from 0.5% to 25% by weight, more preferably 1–10% by weight at temperatures of for example from 10 to 100° C., preferably from 20 to 80° C. and more preferably from 30 to 60° C.

This can be effected by adding the pulverulent or granular decolorizing agent to the reaction mixture and subsequent filtration or by passing the reaction mixture through a bed of the decolorizing agent in the form of any desired suitable moldings.

The decolorizing of the reaction mixture can be effected at any desired stage in the workup process, for example at the stage of the crude reaction mixture or after any prewash, neutralization, wash or solvent removal.

The reaction mixture can further be subjected to a prewash e) and/or a neutralization f) and/or an afterwash g), preferably merely to a neutralization f). If desired, a neutralization f) and a prewash e) can be interchanged in the sequence.

Carboxylic acid B, for example (meth)acrylic acid, and/or catalyst C can be at least partly recovered from the aqueous phase of the washes e) and g) and/or neutralization f) by acidification and extraction with a solvent and reused.

For a pre- or afterwash e) or g), the reaction mixture is treated in a wash apparatus with a wash liquor, for example water or a 5–30% by weight, preferably 5–20% and more preferably 5–15% by weight sodium chloride, potassium chloride, ammonium chloride, sodium sulfate or ammonium sulfate solution, preferably water or sodium chloride solution.

The ratio of reaction mixture to wash liquor is generally in the range from 1:0.1 to 1:1, preferably in the range from 1:0.2 to 1:0.8 and more preferably in the range from 1:0.3 to 1:0.7.

The wash or neutralization can be carried out for example in a stirred container or in other conventional apparatuses for example in a column or a mixer-settler apparatus.

In terms of process engineering, any wash or neutralization in the process according to the present invention can be carried out using conventional extraction and washing processes and apparatuses, for example those described in Ullmann's Encyclopedia of Industrial Chemistry, 6th ed, 1999 Electronic Release, Chapter: Liquid—Liquid Extraction—Apparatus. For example, the choice may be for single- or multi-staged, preferably single-staged, extractions, and also for these in cocurrent or countercurrent mode and preferably in countercurrent mode.

Preference is given to using sieve tray columns, arrangedly or randomly packed columns, stirred vessels or mixer-settler apparatuses and also pulsed columns or columns having rotating internals.

The prewash e) is preferably used whenever metal salts and preferably copper or copper salts are (concomitantly) used as inhibitors.

An afterwash g) may be preferable to remove traces of base or salt traces from the reaction mixture neutralized in f).

By way of neutralization f), the reaction mixture which may have been prewashed and which may still contain small amounts of catalyst and the main amount of excess carboxylic acid, for example (meth)acrylic acid, can be neutralized with a 5–25%, preferably 5–20% and more preferably 5–15% by weight aqueous solution of a base, for example alkali metal or alkaline earth metal oxides, hydroxides, carbonates or bicarbonates, preferably aqueous sodium hydroxide solution, aqueous potassium hydroxide solution, sodium bicarbonate, sodium carbonate, potassium bicarbonate, calcium hydroxide, milk of lime, ammonia gas, ammonia water or potassium carbonate, to which solution 5–15% by weight of sodium chloride, potassium chloride, ammonium chloride or ammonium sulfate may have been added, if desired, more preferably with aqueous sodium hydroxide solution or aqueous sodium hydroxide-sodium chloride solution. The degree of neutralization is preferably in the range from 10 to 80 mol %, more preferably in the range from 20 to 80 mol %, even more preferably in the range from 40 to 80 mol %, based on the acid-functional monomers. This neutralization can take place before and/or during the polymerization, preferably before the polymerization.

The base is added in such a way that the temperature in the apparatus does not rise above 60° C. and is preferably in the range from 20 to 35° C., and the pH is 4–13. The heat of neutralization is preferably removed by cooling the vessel with the aid of internal cooling coils or via jacketed cooling.

The ratio of reaction mixture to neutralizing liquor is generally in the range from 1:0.1 to 1:1, preferably in the range from 1:0.2 to 1:0.8 and more preferably in the range from 1:0.3 to 1:0.7.

With regard to the apparatus, the above statements apply.

h) When a solvent is present in the reaction mixture, it may be substantially removed by distillation. Preferably, any solvent present is removed from the reaction mixture after washing and/or neutralization, but if desired this may also be done prior to the wash or neutralization.

For this, the reaction mixture is admixed with an amount of storage stabilizer, preferably hydroquinone monomethyl ether, such that, after removal of the solvent, 100–500, preferably 200–500 and more preferably 200–400 ppm thereof are present in the target ester (residue).

The distillative removal of the main amount of solvent is effected for example in a stirred tank with jacketed heating and/or internal heating coils under reduced pressure, for example at 20–700 mbar, preferably 30–500 mbar and more preferably 50–150 mbar and 40–80° C. It will be appreciated that the distillation can also be accomplished in a falling-film or thin-film evaporator. For this, the reaction mixture is recirculated, preferably two or more times, through the apparatus under reduced pressure, for example at 20–700 mbar, preferably 30–500 mbar and more preferably 50–150 mbar and 40–80° C.

An inert gas, preferably an oxygen-containing gas, more preferably air or a mixture of air and nitrogen (lean air) may preferably be introduced into the distillation apparatus, for example 0.1–1, preferably 0.2–0.8 and more preferably 0.3–0.7 $m^3/m^3h$, based on the volume of the reaction mixture.

The residual solvent content of the residue is generally below 5% by weight, preferably 0.5–5% and more preferably 1–3% by weight after the distillation.

The removed solvent is condensed and preferably reused.

If necessary, a solvent stripping operation i) can be carried out in addition to or in lieu of the distillation.

For this, the target ester, which still contains small amounts of solvent, is heated to 50–90° C. and preferably 80–90° C. and the remaining amounts of solvent removed with a suitable gas in a suitable apparatus. There are circumstances where a vacuum can be applied in support, if desired.

Examples of useful apparatus include columns of conventional design which contain conventional internals, for example trays, dumped packing or structured packing, preferably dumped packing. Useful column internals include in principle all common internals, for example trays, arranged packing and/or random packing. Preferred trays include bubble trays, sieve trays, valve trays, Thormann trays and/or dual-flow trays, while preferred dumped packings are those of rings, coils, saddles, Raschig, Intos or Pall rings, barrel or Intalox saddles, Top-Pak, etc or braids.

Another possibility here is a falling-film, thin-film or wipe-film evaporator, for example a Luwa, Rotafilm or Sambay evaporator, which may be splash-guarded with a demister for example.

Useful gases-include gases which are inert under the stripping conditions, preferably oxygen-containing gases, more preferably air or mixtures of air and nitrogen (lean air) or water vapor, especially such gases which have been preheated to 50–100° C.

The stripping gas rate is for example in the range from 5 to 20, more preferably in the range from 10 to 20 and most preferably in the range from 10 to 15 m$^3$/m$^3$h, based on the volume of the reaction mixture.

If necessary, the ester can be subjected to a filtration j) at any stage of the workup process, preferably after washing/neutralization and any effected solvent removal, in order that precipitated traces of salts and any decolorizing agent may be removed.

In a conceivable embodiment, the esterification a) of the polyalcohol A with the carboxylic acid B in the presence of at least one esterification catalyst C and of at least one polymerization inhibitor D is carried out in a molar excess of at least 5:1, as indicated above, without a solvent capable of forming an azeotrope with water.

The excess carboxylic acid B is preferably substantially not removed, ie only that fraction of carboxylic acid B is removed from the reaction mixture that is determined by the volatility at the employed temperature, and beyond that no measures are carried out to remove the carboxylic acid, for example no distillative, rectificative, extractive (washing for example), absorptive (for example passing through activated carbon or through ion exchangers) and/or chemical steps such as scavenging of the carboxylic acid with epoxides are carried out.

The extent to which the carboxylic acid B in the reaction mixture is removed from it is preferably not more than 75% by weight, more preferably not more than 50% by weight, even more preferably not more than 25% by weight, especially not more than 10% by weight and most preferably not more than 5% by weight, based on the carboxylic acid B in the reaction mixture after the reaction has ended. In a particularly preferred embodiment, stage b) can be omitted, so that only the fraction of water of reaction and carboxylic acid B is removed from the reaction mixture that is determined by the volatility at the employed temperature. This can preferably be prevented by substantially complete condensation.

Furthermore, the esterification catalyst C used is likewise substantially left in the reaction mixture.

The DIN EN 3682 acid number of the reaction mixture thus obtainable is preferably at least 25 mg of KOH/g of reaction mixture, more preferably in the range from 25 to 80 and most preferably in the range from 25 to 50 mg of KOH/g.

Any pre- or afterwash e) or g) is preferably omitted; merely a filtration step j) can be sensible.

The reaction mixture can subsequently be diluted in step c), in which case it is preferably converted within 6 hours and more preferably within 3 hours to the hydrogel. It may preferably be neutralized in a step f).

The order of the steps c), j) and f) is arbitrary.

The present invention further provides a composition of matter comprising
at least one ester F obtainable by one of the esterification processes described above,
carboxylic acid B and
diluent G.

The composition of matter of the present invention may further comprise
esterification catalyst C in protonated or unprotonated form,
polymerization inhibitor D and also
any solvent E if used in the esterification.

The composition of matter may have been neutralized and have a pH as recited above under f).

When the composition of matter has been neutralized, at least a portion of the carboxylic acids B has been converted into their water-soluble alkali metal, alkaline earth metal or ammonium salts.

A preferred composition of matter comprises
ester F in a fraction from 0.1% to 40% by weight, more preferably from 0.5% to 20%, even more preferably from 1% to 10%, especially from 2% to 5% and specifically from 2% to 4% by weight,
carboxylic acid B at 0.5–99.9% by weight, more preferably 0.5–50% by weight, even more preferably 1–25%, especially 2–15% and specifically from 3% to 5% by weight,
esterification catalyst C at 0–10% by weight, more preferably 0.02–5%, even more preferably 0.05–2.5% by weight and especially 0.1–1% by weight,
polymerization inhibitor D at 0–5% by weight, more preferably 0.01–1.0%, even more preferably 0.02–0.75%, especially 0.05–0.5% and specifically 0.075–0.25% by weight,
solvent E at 0–10% by weight, more preferably 0–5% by weight, even more preferably 0.05–1.5% by weight and especially 0.1–0.5% by weight, with the proviso that the sum total is always 100% by weight, and also
any diluent G ad 100% by weight.

The reaction mixtures obtainable by the above process and compositions of matter according to the present invention can find use
as a radical crosslinker of water-absorbing hydrogels,
as a starting material for producing polymer dispersions,
as a starting material for producing polyacrylates (except hydrogels),
as a paint raw material or
as a cement additive.

Compositions of matter according to the present invention which are particularly useful as radical crosslinkers for water-absorbing hydrogels have a solubility in distilled water at 25° C. of not less than 5% by weight, preferably not less than 10% by weight, more preferably not less than 20% by weight, even more preferably not less than 30% by weight and especially not less than 50% by weight.

k) The reaction mixture from the esterification, including workup steps thereof, where practiced, for example the reaction mixture from f) or, when f) is omitted, from b) or, when b) is omitted, the reaction mixture from a), can optionally be admixed with additional monoethylenically unsaturated compounds N which bear no acid groups but are copolymerizable with the hydrophilic monomers M and can then be polymerized in the presence of at least one radical initiator K and optionally at least one grafting base L to prepare water-absorbing hydrogels.

It may be preferable to conduct 1) to postcrosslink the reaction mixture of k).

Useful hydrophilic monomers M for preparing k) these highly swellable hydrophilic hydrogels include for example acids capable of addition polymerization, such as acrylic acid, methacrylic acid, ethacrylic acid, α-chloroacrylic acid, crotonic acid, maleic acid, maleic anhydride, vinylsulfonic acid, vinylphosphonic acid, maleic acid, maleic anhydride, fumaric acid, itaconic acid, citraconic acid, mesaconic acid, glutaconic acid, aconitic acid, allylsulfonic acid, sulfoethyl acrylate, sulfomethacrylate, sulfopropyl acrylate, sulfopropyl methacrylate, 2-hydroxy-3-acryloyloxypropylsulfonic acid, 2-hydroxy-3-methacryloyloxypropylsulfonic acid, allylphosphonic acid, styrenesulfonic acid, 2-acrylamido-2-methylpropanesulfonic acid, 2-acrylamido-2-methylpropanephosphonic acid and also their amides, hydroxyalkyl esters and amino- or ammonio-containing esters and amides. These monomers can be used alone or mixed with each other. Furthermore water-soluble N-vinylamides and also diallyldimethylammonium chloride. Preferred hydrophilic monomers are compounds of the formula V

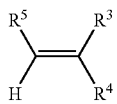

where $R^3$ is hydrogen, methyl or ethyl, $R^4$ is —COOR$^6$, a sulfonyl group, a phosphonyl group, a $(C_1-C_4)$-alkanol-esterified phosphonyl group or a group of the formula VI

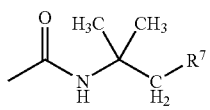

$R^5$ is hydrogen, methyl, ethyl or a carboxyl group, $R^6$ is hydrogen, amino or hydroxy-$(C_1-C_4)$-alkyl, and $R^7$ is a sulfonyl group, a phosphonyl group or a carboxyl group.

Examples of $(C_1-C_4)$-alkanols are methanol, ethanol, n-propanol and n-butanol.

Particularly preferred hydrophilic monomers are acrylic acid and methacrylic acid.

To optimize properties, it can be sensible to use additional monoethylenically unsaturated compounds N which do not bear an acid group but are copolymerizable with the monomers bearing acid groups. Such compounds include for example the amides and nitriles of monoethylenically unsaturated carboxylic acid, for example acrylamide, methacrylamide and N-vinylformamide, N-vinylacetamide, N-methylvinylacetamide, acrylonitrile and methacrylonitrile. Examples of further suitable compounds are vinyl esters of saturated $C_1$- to $C_4$-carboxylic acids such as vinyl formate, vinyl acetate or vinyl propionate, alkyl vinyl ethers having at least 2 carbon atoms in the alkyl group, for example ethyl vinyl ether or butyl vinyl ether, esters of monoethylenically unsaturated $C_3$- to $C_6$-carboxylic acids, for example esters of monohydric $C_1$- to $C_{18}$-alcohols and acrylic acid, methacrylic acid or maleic acid, monoesters of maleic acid, for example methyl hydrogen maleate, N-vinyllactams such as N-vinylpyrrolidone or N-vinylcaprolactam, acrylic and methacrylic esters of alkoxylated monohydric saturated alcohols, for example of alcohols having from 10 to 25 carbon atoms which have been reacted with from 2 to 200 mol of ethylene oxide and/or propylene oxide per mole of alcohol, and also monoacrylic esters and monomethacrylic esters of polyethylene glycol or polypropylene glycol, the molar masses ($M_n$) of the polyalkylene glycols being up to 2000, for example. Further suitable monomers are styrene and alkyl-substituted styrenes such as ethylstyrene or tert-butylstyrene.

These monomers without acid groups may also be used in mixture with other monomers, for example mixtures of vinyl acetate and 2-hydroxyethyl acrylate in any proportion. These monomers without acid groups are added to the reaction mixture in amounts within the range from 0 to 50% by weight, preferably less than 20% by weight.

The crosslinked (co)polymers preferably consist of acid-functional monoethylenically unsaturated monomers which have optionally been converted into their alkali metal or ammonium salts before or after polymerization and of 0–40% by weight based on their total weight of monoethylenically unsaturated monomers which do not bear acid groups.

The production of (meth)acrylic acid (co)polymers, polyacrylic acids and superabsorbents has been extensively described before and therefore is well known, see for example "Modern Superabsorbent Polymer Technology", F. L. Buchholz and A. T. Graham, Wiley-VCH, 1998.

Preference is given to such hydrogels which are obtained by crosslinking addition polymerization or copolymerization of acid-functional monoethylenically unsaturated monomers M or salts thereof.

In the postcrosslinking process, the starting polymer is treated with a postcrosslinker and preferably during or after the treatment postcrosslinked and dried by raising the temperature, the crosslinker preferably being included in an inert solvent. Inert solvents are solvents which substantially do not react either with the starting polymer or with the postcrosslinker. Preference is given to such solvents which do not react chemically with the starting polymer or with the postcrosslinker to an extent of more than 90%, preferably more than 95%, more preferably more than 99% and especially more than 99.5%.

Postcrosslinking 1) and drying m) is preferably carried out at from 30 to 250° C., especially 50–200° C. and most preferably at from 100 to 180° C. The surface postcrosslinking solution is preferably applied by spraying the polymer in suitable spray mixers. After spraying, the polymer powder is thermally dried, and the crosslinking reaction can take place not only before but also during the drying operation. Preference is given to spraying a solution of the crosslinker in reaction mixers or mixing and drying ranges such as for example Lödige mixers, BEPEX mixers, NAUTA mixers, SHUGGI mixers or PROCESSALL. It is moreover also possible to use fluidized bed dryers.

The drying operation can take place in the mixer itself, by heating of the shell or by blowing in hot air. Also suitable is a downstream dryer such as for example a shelf dryer, a rotary tube oven or a heatable screw. But it is also possible to utilize an azeotropic distillation as drying technique, for example. The preferred residence time at this temperature in the reaction mixer or dryer is below 60 min and more preferably below 30 min.

Preference is given to the above processes wherein the starting polymer is a polymeric acrylic acid or a polyacrylate, especially a polymeric acrylic acid or a polyacrylate obtained by free-radical polymerization using a polyfunctional ethylenically unsaturated radical crosslinker.

Preference is given to such processes wherein the composition of matter containing radical crosslinkers, ie the ester F, and diluents G in a ratio of 0.1–20% by weight and especially 0.5–10% by weight based on the mass of the starting polymer is used.

Preference is given to such processes wherein the radical crosslinker is used in a dose of 0.01–5.0% by weight, preferably 0.02–3.0% by weight, more preferably 0.03–2.5% by weight, especially 0.05–1.0% and specifically from 0.1% to 0.75% by weight based on the starting polymer.

The present invention also provides polymers prepared by one of the processes mentioned above and for their use in hygiene articles, packaging materials and nonwovens and also for the use of an abovementioned composition of matter for producing crosslinked or thermally crosslinkable polymers, especially in paints and varnishes.

The highly swellable hydrophilic hydrogels to be used (starting polymers) are in particular polymers of (co)polymerized hydrophilic monomers M, graft (co)polymers of one or more hydrophilic monomers M on a suitable grafting base L, crosslinked cellulose or starch ethers or natural products capable of swelling in aqueous fluids, for example guar derivatives. These hydrogels are known to one skilled in the art and are described for example in U.S. Pat. No. 4,286,082, DE-C-27 06 135, U.S. Pat. No. 4,340,706, DE-C-37 13 601, DE-C-28 40 010, DE-A-43 44 548, DE-A-40 20 780, DE-A-40 15 085, DE-A-39 17 846, DE-A-38 07 289, DE-A-35 33 337, DE-A-35 03 458, DE-A-42 44 548, DE-A-42 19 607, DE-A-40 21 847, DE-A-38 31 261, DE-A-03 51 086, DE-A-31 18 172, DE-A-30 28 043, DE-A-44 18 881, EP-A-0 801 483, EP-A-0 455 985, EP-A-0 467 073, EP-A-0 312 952, EP-A-0 205 874, EP-A-0 499 774, DE-A 26 12 846, DE-A-40 20 780, EP-A-0 20 5674, U.S. Pat. No. 5,145,906, EP-A-0 530 438, EP-A-0 670 073, U.S. Pat. Nos. 4,057,521, 4,062,817, 4,525,527, 4,295,987, 5,011,892, 4,076,663 or 4,931,497. Also of particular suitability are highly swellable hydrogels from a manufacturing operation as described in WO 01/38402 and also highly swellable inorganic/organic hybrid hydrogels as described in DE 198 54 575. The content of the aforementioned patent documents, especially the hydrogels obtained by the processes, is incorporated herein by reference.

Suitable grafting bases L for hydrophilic gels obtainable by graft copolymerization of olefinically unsaturated acids can be of natural or synthetic origin. Examples are starch, cellulose, cellulose derivatives and also other polysaccharides and oligosaccharides, polyalkylene oxides, especially polyethylene oxides and polypropylene oxides, and also hydrophilic polyesters.

The water-absorbing polymer is obtainable by free-radical graft copolymerization of acrylic acid or acrylate onto a water-soluble polymer matrix. Nonlimiting examples of suitable water-soluble polymer matrices are alginates, polyvinyl alcohol and polysaccharides such as starch for example. A graft copolymerization for the purposes of the present invention utilizes a polyfunctional-ethylenically unsaturated radical crosslinker.

The water-absorbing polymer can be an organic/inorganic hybrid polymer formed from a polymeric acrylic acid or polyacrylate on the one hand and a silicate, aluminate or aluminosilicate on the other. More particularly, the polymeric acrylic acid or polyacrylate used may be obtained by free-radical polymerization using a polyfunctional ethylenically unsaturated radical crosslinker and formed using a water-soluble silicate or soluble aluminate or mixture thereof.

Preferred hydrogels are in particular polyacrylates, polymethacrylates and also the U.S. Pat. Nos. 4,931,497, 5,011, 892 and 5,041,496 graft polymers. Very particularly preferred hydrogels are the kneader polymers described in WO 01/38402 and the polyacrylate-based organic/inorganic hybrid hydrogels described in DE 198 545 75.

The substances prepared according to the present invention, which are useful as radical crosslinkers in hydrogels, can be used alone or in combination with other crosslinkers, for example internal or surface crosslinkers, for example the following:

Suitable crosslinkers are in particular methylenebisacrylamide, methylenebismethacrylamide, esters of unsaturated mono- or polycarboxylic acids with polyols, such as diacrylate or triacrylate, for example butanediol diacrylate, butanediol dimethacrylate, ethylene-glycol diacrylate, ethylene glycol dimethacrylate, and also trimethylolpropane triacrylate and allyl compounds such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A-0 343 427. However, particular preference for use in the process of the present invention is given to hydrogels prepared using polyallyl ethers as crosslinkers and by acidic homopolymerization of acrylic acid. Suitable crosslinkers are pentaerythritol triallyl ether, pentaerythritol tetraallyl ether, polyethylene glycol diallyl ether, monoethylene glycol diallyl ether, glycerol diallyl ether, glycerol triallyl ether, polyallyl ethers based on sorbitol and also ethoxylated variants thereof. Particularly preferred crosslinkers further include polyethylene glycol diacrylates, ethoxylated derivatives of trimethylolpropane triacrylate, for example Sartomer SR 9035, and also ethoxylated derivatives of glycerol diacrylate and glycerol triacrylate. It is obviously also possible to use mixtures of the above crosslinkers.

Very particular preference is given to hydrogels prepared using an ester F prepared according to the present invention as a radical crosslinker.

The water-absorbing polymer is preferably a polymeric acrylic acid or a polyacrylate. This water-absorbing polymer can be prepared by a process known from the literature. Preference is given to polymers which contain crosslinking comonomers (0.001–10 mol %), but very particular preference is given to polymers which were obtained by free-radical polymerization and where a polyfunctional ethylenically unsaturated radical crosslinker was used.

The highly swellable hydrophilic hydrogels are preparable by addition polymerization processes known per se. Preference is given to the addition polymerization in aqueous solution conducted as a gel polymeization. It involves, as stated above, dilute, preferably aqueous and more preferably 15–50% by weight aqueous, solutions of one or more hydrophilic monomers and optionally of a suitable grafting base L being polymerized in the presence of a free-radical initiator by utilizing the Trommsdorff-Norrish effect (Makromol. Chem. 1, 169 (1947)) preferably without mechanical mixing. The polymerization reaction may be carried out at from 0° C. to 150° C., and preferably at from 10° C. to 100° C., not only at atmospheric pressure but also at superatmospheric or reduced pressure. Typically, the polymerization can also be carried out in a protective gas atmosphere, preferably under nitrogen. The addition polymerization may be induced using high-energy electromagnetic rays or the customary chemical polymerization initiators K, for example organic peroxides, such as benzoyl peroxide, tert-butyl hydroperoxide, methyl ethyl ketone peroxide, cumene hydroperoxide, azo compounds such as azobisisobutyronitrile and also inorganic peroxy compounds such as $(NH_4)_2S_2O_8$, $K_2S_2O_8$ or $H_2O_2$.

They can if desired be used in combination with reducing agents such as ascorbic acid, sodium hydrogensulfite and iron(II) sulfate or redox systems where the reducing component included is an aliphatic and aromatic sulfinic acid, such as benzenesulfinic acid and toluene sulfinic acid or derivatives thereof, for example Mannich adducts of sulfinic acids, aldehydes and amino compounds, as described in DE-C-1 301 566. The performance properties of the polymers can be further improved by postheating the polymer gels in the temperature range from 50° to 130° C. and preferably from 70° to 100° C. for several hours.

The gels obtained are neutralized to the extent of 0–100 mol %, preferably 25–100 mol % and more preferably 50–85 mol % based on monomer used, for which the customary neutralizing agents can be used, preferably alkali metal hydroxides, alkali metal oxides or the corresponding alkali metal carbonates, but more preferably sodium hydroxide, sodium carbonate and sodium bicarbonate.

Neutralization is typically achieved by mixing the neutralizing agent as an aqueous solution or else preferably as a solid into the gel. For this, the gel is mechanically comminuted, for example by means of a meat grinder, and the neutralizing agent is sprayed on, scattered on or poured on and then carefully mixed in. The gel mass obtained can then be repeatedly passed through the meat grinder for homogenization. The neutralized gel mass is then dried with a belt or can dryer until the residual moisture content is preferably below 10% by weight and especially below 5% by weight.

The addition polymerization as such can also be carried out by any other process described in the literature. More particularly, the neutralization of the acrylic acid can also be carried out prior to the polymerization, as described above in step f). The polymerization can then be carried out in a conventional belt reactor or a kneading reactor continuously or else batchwise. When the polymerization is carried out in a belt reactor, initiation by electromagnetic radiation and preferably by UV radiation or alternatively initiation by means of a redox initiator system is particularly preferred. Very particular preference is also given to a combination of the two methods of initiation: electromagnetic radiation and chemical redox initiator system simultaneously.

n) The dried hydrogel can then be ground and sieved, in which case it is customary to use roll mills, pin mills or vibratory mills for the grinding. The preferred particle size of the sieved hydrogel is preferably in the range 45–1000 μm, more preferably at 45–850 μm, even more preferably at 200–850 μm, and most preferably at 300–850 μm. These ranges preferably cover 80% by weight of the particles and especially 90% by weight of the particles. The size distribution can be determined using established laser methods.

The present invention further provides crosslinked hydrogels which contain at least one hydrophilic monomer M in copolymerized form and have been crosslinked using an ester F of a polyalcohol A with at least one ethylenically unsaturated carboxylic acid B. The ester can be prepared in a manner according to the present invention or in a prior art manner and is preferably prepared in a manner according to the present invention.

Useful esters F include compounds as described above. Polyalcohols A and ethylenically unsaturated carboxylic acids B are likewise those as described above.

Esters F are preferred where the polyalcohol A is selected from the group consisting of a polyol which bears an additional functionality, said additional functionality being at least one ether, carboxyl or $C_1$–$C_4$-alkyloxycarbonyl function, sugar alcohols, partially alkoxylated sugar alcohols, polyesterols, partially or fully alkoxylated polyesterols and partially or fully hydrolyzed alkoxylated polyesterols, as described above in each case.

Particular preference is given to esters F where the polyalcohol A is selected from the group consisting of ditrimethylolpropane, dipentaerythritol, dimethylolpropionic acid and dimethylolbutyric acid.

Preferred esters F further include those of the formula VII as defined above where y is independently in each occurrence
  for x=2 a number greater than 8, preferably more than 10, more preferably more than 12 and especially at least 15, and
  where x=3 or greater a number greater than 7, preferably more than 9, more preferably more than 12 and especially at least 15.

Preference is likewise given to esters F of the formula VII as defined above where y is independently in each occurrence up to 6, more preferably up to 4 and most preferably 4.

It is also possible to use esters F of the formula VII as defined above where y is 0, 1 or 2 for x=2 and 0 or 1 for x=3.

The polyalcohols A of the formula VII in the esters F which are used as crosslinkers in the aforementioned hydrogels can each have been ethoxylated, propoxylated or mixedly ethoxylated and propoxylated and especially exclusively ethoxylated, ie $R^{10}$ in the formula VII can for example be independently in each occurrence hydrogen and/or methyl and especially exclusively hydrogen.

Particular preference for use as esters F of the formula VII is given to esters F of a polyalcohol A with at least one ethylenically unsaturated carboxylic acid B where the polyalcohol A is from triply to quadruply ethoxylated glycerol or is a trimethylolpropane or pentaerythritol which has been quadruply ethoxylated per hydroxyl group.

The CRC value [g/g] of the hydrogel-forming polymers according to the present invention can be measured by the methods indicated in the description and is preferably above 15, especially 16, 18, 20, 22, 24, or higher, more preferably 25, especially 26, 27, 28, 29, even more preferably 30, 31, 32, 33, 34, 35, 36, 37 or higher.

The AUL 0.7 psi value [g/g] of the hydrogel-forming polymers according to the present invention can be measured by the methods indicated in the description part and is preferably above 8, especially 9, 10, 11, 12, 13, 14 or higher, more preferably 15 especially 16, 17, 18, 19, or higher, even more preferably above 20, especially 21, 22, 23, 24, 25, 26, 27, 28, or higher.

The AUL 0.5 psi value [g/g] of the hydrogel-forming polymers according to the present invention can be measured by the methods indicated in the description part and is preferably above 8, especially 9, 10, 11, 12, 13, 14 or higher, more preferably 15 especially 16, 17, 18, 19, or higher, even more preferably above 20, especially 21, 22, 23, 24, 25, 26, 27, 28, or higher.

Application and Use of the Hydrogel-Forming Polymers According to the present invention The present invention further relates to the use of the abovementioned hydrogel-forming polymers in hygiene articles comprising
(P) a liquid-pervious topsheet
(O) a liquid-impervious backsheet
(R) a core positioned between (P) and (O) and comprising
  10–100% by weight of the hydrogel-forming polymer according to the present invention 0–90% by weight of hydrophilic fiber material
  preferably 20–100% by weight of the hydrogel-forming polymer according to the present invention, 0–80% by weight of hydrophilic fiber material more preferably 30–100% by weight of the hydrogel-forming polymer according to the present invention, 0–70% by weight of hydrophilic fiber material even more preferably 40–100% by weight of the hydrogel-forming polymer according to the present invention, 0–60% by weight of hydrophilic fiber material yet even more preferably 50–100% by weight of the hydrogel-forming polymer according to the present invention, 0–50% by weight of hydrophilic fiber material particularly preferably 60–100% by weight of the hydrogel-forming polymer according to the present invention, 0–40% by weight of hydrophilic fiber material especially preferably 70–100% by weight of the hydrogel-forming polymer according to the present invention, 0–30% by weight of hydrophilic fiber material extremely preferably 80–100% by weight of the hydrogel-forming polymer according to the present invention, 0–20% by weight of hydrophilic fiber material most preferably 90–100% by weight of the hydrogel-forming polymer according to the present invention, 0–10% by weight of hydrophilic fiber material (S) optionally a tissue layer positioned directly above and below said core (R), and (T) optionally an acquisition layer positioned between (P) and (R).

The percentages are to be understood so that in the case of 10–100% by weight, 11%, 12%, 13%, 14%, 15%, 16%, 17%, 18%, 19% up to in each case 100% by weight of hydrogel-forming polymer according to the present invention and all intermediate % (for example 12.2%) are possible and correspondingly hydrophilic fiber material from 0% to in each case 89%, 88%, 87%, 86%, 85%, 83%, 82%, 81% by weight and intermediate percentages (for example 87.8%) are possible. When further materials are present in the core, the percentages of polymer and fiber decrease accordingly. The same applies to the preferred ranges, for example in the case of extremely preferable 81%, 82%, 83%, 84%, 85%, 86%, 87%, 88%, 89% by weight can be present for the hydrogel-forming polymer according to the present invention and correspondingly 19%, 18%, 17%, 16%, 15%, 14%, 13%, 12%, 11% by weight for the fiber material. Thus, 20%, 21%, 22%, 0.23%, 24%, 25%, 26%, 27%, 28%, 29% to 100% by weight of the hydrogel-forming polymer according to the present invention can be present in the preferred range, 30%, 31%, 32%, 33%, 34%, 35%, 36%, 37%, 38%, 39% to 100% by weight can be present for the hydrogel-forming polymer according to the present invention, in the more preferred range, 40%, 41%, 42%, 43%, 44%, 45%, 46%, 47%, 48%, 49% to 100% by weight can be present for the hydrogel-forming polymer according to the present invention, in the even more preferred range, 50%, 51%, 52%, 53%, 54%, 55%, 56%, 57%, 58%, 59% to 100% by weight can be present for the hydrogel-forming polymer according to the present invention, in the yet even more preferred range, 60%, 61%, 62%, 63%, 64%, 65%, 66%, 67%, 68%, 69% to 100% by weight can be present for the hydrogel-forming polymer according to the present invention, in the particularly preferred range, 70%, 71%, 71%, 72%, 73%, 74%, 75%, 76%, 77%, 78%, 79% to 100% by weight can be present for the hydrogel-forming polymer according to the present invention in the especially preferred range, and 90%, 91%, 92%, 93%, 94%, 95%, 96%, 97%, 98%, 99% or 100% by weight can be present for the hydrogel-forming polymer according to the present invention in the most preferred range.

Hygiene articles for the purposes of the present invention include not only incontinence pads and incontinence briefs for adults but also diapers for infants.

The liquid-pervious topsheet (P) is the layer which is in direct contact with the skin of the wearer. Its material comprises customary synthetic or manufactured fibers or films of polyesters, polyolefins, rayon or natural fibers such as cotton. In the case of non-woven materials the fibers are generally joined together by binders such as polyacrylates. Preferred materials are polyesters, rayon and blends thereof, polyethylene and polypropylene. Examples of liquid-pervious layers are described in WO 99/57355 A1, EP 102 388 3 A2.

The liquid-impervious layer (O) is generally a sheet of polyethylene or polypropylene.

The core (R) includes not only the hydrogel-forming polymer according to the present invention but also hydrophilic fiber material. By hydrophilic is meant that aqueous fluids spread quickly over the fiber. The fiber material is usually cellulose, modified cellulose, rayon, polyester such as polyethylene terephthalate. Particular preference is given to cellulose fibers such as pulp. The fibers generally have a diameter of 1–200 μm and preferably 10–100 μm, and also have a minimum length of 1 mm.

Diaper construction and shape is common knowledge and described for example in WO 95/26 209 page 66 line 34 to page 69 line 11, DE 196 04 601 A1, EP-A-0 316 518 and EP-A-0 202 127. Diapers and other hygiene articles are generally also described in WO 00/65084, especially at pages 6–15, WO 00/65348, especially at pages 4–17, WO 00/35502, especially pages 3–9, DE 19737434, WO 98/8439. Hygiene articles for feminine care are described in the following references. The subject hydrogel-forming polymers capable of absorbing aqueous fluids can be used there. Feminine care references: WO 95/24173: Absorption Article for Controlling Odour, WO 91/11977: Body Fluid Odour Control, EP 389023: Absorbent Sanitary Articles, WO 94/25077: Odour Control Material, WO 97/01317: Absorbent Hygienic Article, WO 99/18905, EP 834297, U.S. Pat. No. 5,762,644, U.S. Pat. No. 5,895,381, WO 98/57609, WO 2000/065083, WO 2000/069485, WO 2000/069484, WO 2000/069481, U.S. Pat. No. 6,123,693, EP 1104666, WO 2001/024755, WO 2001/000115, EP 105373, WO 2001/041692, EP 1074233. Tampons are described in the following references: WO 98/48753, WO 98/41179, WO 97/09022, WO 98/46182, WO 98/46181, WO 2001/043679, WO 2001/043680, WO 2000/061052, EP 1108408, WO 2001/033962, DE 200020662, WO 2001/001910, WO 2001/001908, WO 2001/001909, WO 2001/001906, WO 2001/001905, WO 2001/24729. Incontinence articles are described in the following references: Disposable Absorbent Article for Incontinent Individuals: EP 311344 description-pages 3–9; Disposable Absorbent Article: EP 850623; Absorbent Article: WO 95/26207; Absorbent Article: EP 894502; Dry Laid Fibrous Structure: EP 850 616; WO 98/22063; WO 97/49365; EP 903134; EP 887060; EP 887059; EP 887058; EP 887057; EP 887056; EP 931530; WO 99/25284; WO 98/48753. Feminine care and incontinence articles are described in the following references: Catamenial Device: WO 93/22998 description pages 26–33; Absorbent Members for Body Fluids: WO 95/26209 description pages 36–69; Disposable Absorbent Article: WO 98/20916 description pages 13–24; Improved Composite Absorbent Structures: EP 306262 description pages 3–14; Body Waste Absorbent Article: WO 99/45973. These references and the references therein are hereby expressly incorporated herein.

The hydrogel-forming polymers according to the present invention are very useful as absorbents for water and aqueous fluids, so that they may be used with advantage as a water retainer in market gardening, as a filter aid and particularly as an absorbent component in hygiene articles such as diapers, tampons or sanitary napkins.

Incorporation and Fixation of the Highly Swellable Hydrogels According to the Present Invention In addition to the above-described highly swellable hydrogels, the absorbent composition of the present invention includes constructions which include highly swellable hydrogels or to which they are fixed. Any construction is suitable that is capable of accommodating highly swellable hydrogels and of being integrated into the absorption layer. A multiplicity of such compositions is already known and described in detail in the literature. A construction for installing the highly swellable hydrogels can be for example a fiber matrix consisting of a cellulose fiber mixture (air-laid web, wet laid web) or synthetic polymer fibers (meltblown web, spunbonded web) or else of a fiber blend of cellulose fibers and synthetic fibers. Possible fiber materials are detailed in the chapter which follows. The air-laid web process is described for example in WO 98/28 478.

Furthermore, open-celled foams or the like may be used to install highly swellable hydrogels.

Alternatively, such a construction can be the result of fusing two individual layers to form one or better a multiplicity of chambers which contain the highly swellable hydrogels. Such a chamber system is described in detail in EP 0 615 736 A1 page 7 lines 26 et seq.

In this case, at least one of the two layers should be water pervious. The second layer may either be water pervious or water impervious. The layer material used may be tissues or other fabric, closed or open-celled foams, perforated films, elastomers or fabrics composed of fiber material. When the absorbent composition consists of a construction of layers, the layer material should have a pore structure whose pore dimensions are small enough to retain the highly swellable hydrogel particles. The above examples of the construction of the absorbent composition also include laminates composed of at least two layers between which the highly swellable hydrogels are installed and fixed.

Generally it is possible to fix hydrogel particles within the absorbent core to improve dry and wet integrity. Dry and wet integrity describes the ability to install highly swellable hydrogels into the absorbent composition in such a way that they withstand external forces not only in the wet but also in the dry state and highly swellable polymer does not dislocate or spill out. The forces referred to are especially mechanical stresses as occur in the course of moving about while wearing the hygiene article or else the weight pressure on the hygiene article in the case of incontinence especially. As to fixation, one skilled in the art knows a multiplicity of possibilities. Examples such as fixation by heat treatment, addition of adhesives, thermoplastics, binder materials are noted in WO 95/26 209 page 0.37 line 36 to page 41 line 14. The cited passage is thus part of this invention. Methods for enhancing wet strength are also to be found in WO 2000/36216 A1.

Furthermore, the absorbent composition may comprise a base material, for example a polymer film on which the highly swellable hydrogel particles are fixed. The fixing may be effected not only on one side but also on both sides. The base material can be water pervious or water impervious.

The above constructions of the absorbent composition incorporate the highly swellable hydrogels at a weight fraction of from 10–100% by weight, preferably 20–100% by weight, more preferably 30–100% by weight, even more preferably 40–100% by weight, much more preferably 50–100% by weight, particularly preferably 60–100% by weight, especially preferably 70–100% by weight, extremely preferably 80–100% by weight and most preferably 90–100% by weight, based on the total weight of the construction and of the highly swellable hydrogels.

Fiber Materials of the Absorbent Composition

The structure of the present composition according to the invention may be based on various fiber materials, which are used as a fiber network or matrices. The present invention includes not only fibers of natural origin (modified or unmodified) but also synthetic fibers.

A detailed overview of examples of fibers which can be used in the present invention is given in WO 95/26 209 page 28 line 9 to page 36 line 8. The cited passage is thus part of this invention.

Examples of cellulose fibers include cellulose fibers which are customarily used in absorption products, such as fluff pulp and cellulose of the cotton type. The materials (soft- or hardwoods), production processes such as chemical pulp, semichemical pulp, chemothermomechanical pulp (CTMP) and bleaching processes are not particularly restricted. For instance, natural cellulose fibers such as cotton, flax, silk, wool, jute, ethylcellulose and cellulose acetate are used.

Suitable synthetic fibers are produced from polyvinyl chloride, polyvinyl fluoride, polytetrafluoroethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and polyethylene-polypropylene bicomponent fibers, polyester fibers, such as polyethylene terephthalate fibers (DACRON® or KODEL®), copolyesters, polyvinyl acetate, polyethyl vinyl acetate, polyvinyl chloride, polyvinylidene chloride, polyacrylics, polyamides, copolyamides, polystyrene and copolymers of the aforementioned polymers and also bicomponent fibers composed of polyethylene terephthalate-polyethylene-isophthalate copolymer, polyethyl vinyl acetate/polypropylene, polyethylene/polyester, polypropylene/polyester, copolyester/polyester, polyamide fibers (nylon), polyurethane fibers, polystyrene fibers and polyacrylonitrile fibers. Preference is given to polyolefin fibers, polyester fibers and their bicomponent fibers. Preference is further given to thermally adhesive bicomponent fibers composed of polyolefin of the core-sheath type and side-by-side type on account of their excellent dimensional stability following fluid absorption.

The synthetic fibers mentioned are preferably used in combination with thermoplastic fibers. In the course of the heat treatment, the latter migrate to some extent into the matrix of the fiber material present and so constitute bond sites and renewed stiffening elements on cooling. Additionally the addition of thermoplastic fibers means that there is an increase in the present pore dimensions after the heat treatment has taken place. This makes it possible, by continuous addition of thermoplastic fibers during the formation of the absorbent core, to continuously increase the fraction of thermoplastic fibers in the direction of the topsheet, which results in a similarly continuous increase in the pore sizes. Thermoplastic fibers can be formed from a multiplicity of thermoplastic polymers which have a melting point of less than 190° C., preferably in the range from 75° C. to 175° C. These temperatures are too low for damage to the cellulose fibers to be likely.

Lengths and diameters of the above-described synthetic fibers are not particularly restricted, and generally any fiber from 1 to 200 mm in length and from 0.1 to 100 denier (gram per 9000 meters) in diameter may preferably be used. Preferred thermoplastic fibers are from 3 to 50 mm in length, particularly preferred thermoplastic fibers are from 6 to 12 mm in length. The preferred diameter for the thermoplastic fiber is in the range from 1.4 to 10 decitex, and the range from 1.7 to 3.3 decitex (gram per 10000 meters) is particularly preferred. The form of the fiber may vary; examples include woven types, narrow cylindrical types, cut/chopped yarn types, staple fiber types and continuous filament fiber types.

The fibers in the absorbent composition of the present invention can be hydrophilic and/or hydrophobic. According to the definition of Robert F. Gould in the 1964 American Chemical Society publication "Contact angle, wettability and adhesion", a fiber is referred to as hydrophilic when the contact angle between the liquid and the fiber (or the fiber surface) is less than 90° or when the liquid tends to spread spontaneously on the same surface. The two processes are generally coexistent. Conversely, a fiber is termed hydrophobic when a contact angle of greater than 90° is formed and no spreading is observed.

Preference is given to using hydrophilic fiber material. Particular preference is given to using fiber material which is weakly hydrophilic on the body side and most hydrophilic in the region surrounding the highly swellable hydrogels. In the manufacturing process, layers having different hydrophilicities are used to create a gradient which channels impinging fluid to the hydrogel, where it is ultimately absorbed.

Suitable hydrophilic fibers for use in the absorbent composition of the present invention include for example cellulose fibers, modified cellulose fibers, rayon, polyester fibers, for example polyethylene terephthalate (DACRON®), and hydrophilic nylon (HYDROFIL®). Suitable hydrophilic fibers may also be obtained by hydrophilicizing hydrophobic fibers, for example the treatment of thermoplastic fibers obtained from polyolefins (e.g. polyethylene or polypropylene, polyamides, polystyrenes, polyurethanes, etc.) with surfactants or silica. However, for cost reasons and ease of availability, cellulosic fibers are preferred.

The highly swellable hydrogel particles are embedded into the fiber material described. This can be done in various ways, for example by using the hydrogel material and the fibers together to create an absorbent layer in the form of a matrix, or by incorporating highly swellable hydrogels into fiber mixture layers, where they are ultimately fixed, whether by means of adhesive or lamination of the layers.

The fluid-acquiring and -distributing fiber matrix may comprise synthetic fiber or cellulosic fiber or a mixture of synthetic fiber and cellulosic fiber, in which case the mixing ratio may vary from (100 to 0) synthetic fiber: (0 to 100) cellulosic fiber. The cellulosic fibers used may additionally have been chemically stiffened to increase the dimensional stability of the hygiene article.

The chemical stiffening of cellulosic fibers may be provided in different ways. A first way of providing fiber stiffening is by adding suitable coatings to the fiber material. Such additives include for example polyamide-epichlorohydrin coatings (Kymene® 557H, Hercoles, Inc. Wilmington, Del., USA), polyacrylamide coatings (described in U.S. Pat. No. 3,556,932 or as the Parez® 631 NC commercial product from American Cyanamid Co., Stamford, Conn., USA), melamine-formaldehyde coatings and polyethyleneimine coatings.

Cellulosic fibers may also be chemically stiffened by chemical reaction. For instance, suitable crosslinker substances may be added to effect crosslinking taking place within the fiber. Suitable crosslinker substances are typical substances used for crosslinking monomers including but not limited to $C_2$–$C_8$-dialdehydes, $C_2$–$C_8$-monoaldehydes having acid functionality and in particular $C_2$–$C_9$-polycarboxylic acids. Specific substances from this series are for example glutaraldehyde, glyoxal, glyoxylic acid, formaldehyde and citric acid. These substances react with at least 2 hydroxyl groups within any one cellulose chain or between two adjacent cellulose chains within any one cellulose fiber. The crosslinking causes a stiffening of the fibers, to which greater dimensional stability is imparted as a result of this treatment. In addition to their hydrophilic character, these fibers exhibit uniform combinations of stiffening and elasticity. This physical property makes it possible to retain the capillary structure even under simultaneous contact with fluid and compressive forces and to prevent premature collapse.

Chemically crosslinked cellulose fibers are known and described in WO 91/11162, U.S. Pat. Nos. 3,224,926, 3,440,135, 3,932,209, 4,035,147, 4,822,453, 4,888,093, 4,898,642 and 5,137,537. The chemical crosslinking imparts stiffening to the fiber material, which is ultimately reflected in improved dimensional stability for the hygiene article as a whole. The individual layers are joined together by methods known to one skilled in the art, for example intermelting by heat treatment, addition of hot-melt adhesives, latex binders, etc.

Methods of Making the Absorbent Composition

The absorbent composition is composed of constructions which contain highly swellable hydrogels and the highly swellable hydrogels which are present in said constructions or fixed thereto.

Examples of processes to obtain an absorbent composition comprising for example a base material to which highly swellable hydrogels are fixed on one or both sides are known and included by the invention but not limited thereto.

Examples of processes to obtain an absorbent composition comprising for example a fiber material blend of synthetic fibers (a) and cellulose fibers (b) embedded in highly swellable hydrogels (c), the blend ratio varying from (100 to 0) synthetic fiber: (0 to 100) cellulose fiber, include (1) a process where (a), (b) and (c) are mixed together at one and the same time, (2) a process where a mixture of (a) and (b) is mixed into (c), (3) a process where a mixture of (b) and (c) is mixed with (a), (4) a process where a mixture of (a) and (c) is mixed into (b), (5) a process where (b) and (c) are mixed and (a) is continuously metered in, (6) a process where (a) and (c) are mixed and (b) is continuously metered in, and (7) a process where (b) and (c) are mixed separately into (a). Of these examples, processes (1) and (5) are preferred. The apparatus used in this process is not particularly restricted and any customary apparatus known to one skilled in the art can be used.

The absorbent composition obtained in this way can optionally be subjected to a heat treatment, so that an absorption layer having excellent dimensional stability in the moist state is obtained. The heat treatment process is not particularly restricted. Examples include heat treatment by feeding hot air or infrared irradiation. The temperature of the heat treatment is in the range from 60° C. to 230° C., preferably from 100° C. to 200° C., particularly preferably from 100° C. to 180° C.

The duration of the heat treatment depends on the type of synthetic fiber, its amount and the hygiene article production rate. Generally the duration of the heat treatment is in the range from 0.5 second to 3 minutes, preferably from 1 second to 1 minute.

The absorbent composition is generally provided for example with a liquid-pervious topsheet and a liquid-impervious backsheet. Furthermore, leg cuffs and adhesive tabs are attached to finalize the hygiene article. The materials and types of pervious topsheet and impervious backsheet and of the leg cuffs and adhesive tabs are known to one skilled in the art and are not particularly restricted. Examples thereof may be found in WO 95/26 209.

The present invention is advantageous in that the esters F, which are useful as crosslinkers, do not have to be purified after they have been formed and particularly in that the carboxylic acid B, for example acrylic acid, does not have to be removed, since it is generally a monomer for forming the hydrogels.

EXPERIMENTAL PART

Parts per million and percentages are by weight, unless otherwise stated.

The example which follows illustrates the process of the present invention.

EXAMPLES

Production of crude acrylate esters useful as SAP-crosslinkers

SAP-crosslinkers are prepared in the examples by esterifying polyethers with acrylic acid by removing water in an azeotropic distillation. The esterification catalyst in the examples is sulfuric acid. The reactants are introduced in the examples as initial charge in methylcyclohexane entrainer together with a stabilizer mixture consisting of hydroquinone monomethyl ether, triphenyl phosphite and hypophosphorous acid. The reaction mixture is then heated to about 98° C. until the azeotropic distillation starts. During the azeotropic distillation, the temperature in the reaction mixture rises. The amount of water removed is determined. The distillation is discontinued once at least the theoretical amount of water has been removed. Subsequently the entrainer is removed in a vacuum distillation. The product is cooled and used as a crosslinker in SAP production.

Conversion and yield of the reaction is not precisely determined because the water removed in the esterification also contains acrylic acid and acrylic acid is also removed during the vacuum distillation of the entrainer. Similarly, the crude ester still contains free acrylic acid which is titrated together with the catalyst (acid number).

Parts are by weight, unless otherwise stated.
Production of Ester
Acid numbers were determined in accordance with DIN EN 3682.

Example 1

(Polyethylene Glycol 400 Diacrylate)

740 parts of polyethylene glycol having an average molar mass of about 400 (Pluriol 400®, BASF AG) were esterified with 320 parts of acrylic acid and 5 parts of sulfuric acid in 354 parts of methylcyclohexane. The assistants used were 3 parts of hydroquinone monomethyl ether, 1 part of triphenyl phosphite and 1 part of hypophosphorous acid. 65 parts of water were removed before the entrainer was removed by vacuum distillation. The product was purified through K300 filter. The acid number was 50.4 mg of KOH/g and was adjusted to 99 mg of KOH/g by addition of 72 parts of acrylic acid. The viscosity of the slightly yellowish product (iodine color number 1) was 91 mPas.

Example 2

(Polyethylene Glycol 600 Diacrylate)

810 parts of polyethylene glycol having an average molar mass of about 600 (Pluriol® 600, BASF AG) were esterified with 234 parts of acrylic acid and 5 parts of sulfuric acid in 448 parts of methylcyclohexane. The assistants used were 3 parts of hydroquinone monomethyl ether, 1 part of triphenyl phosphite and 1 part of hypophosphorous acid. 40 parts of water were removed before the entrainer was removed by vacuum distillation. The product was purified through K300 filter. The acid number was 54 mg of KOH/g and was adjusted to 100 mg of KOH/g by addition of 70 parts of acrylic acid. The viscosity of the slightly yellowish product was 100 mPas.

Example 3

(About 3-tuply, ie Singly Per Hydroxyl Group, Ethoxylated TMP Triacrylate)

579 parts of 3-tuply ethoxylated trimethylolpropane are esterified with 562 parts of acrylic acid and 5 parts of sulfuric acid in 380 parts of methylcyclohexane. The assistants used were 3 parts of hydroquinone monomethyl ether, 1 part of triphenyl phosphite and 1 part of hypophosphorous acid. 125 parts of water were removed before the entrainer was removed by vacuum distillation. The product was purified through K300 filter. The acid number was 38 mg of KOH/g. The viscosity of the almost colorless product (iodine color number 0–1) was 200 mPas.

Example 4

(About 7-tuply, Per Molecule of TMP, Ethoxylated TMP Triacrylate)

681 parts of 7-tuply ethoxylated trimethylolpropane (Polyol TP 70®, Perstorp) were esterified with 414 parts of acrylic acid and 5 parts of sulfuric acid in 365 parts of methylcyclohexane. The assistants used were 3 parts of hydroquinone monomethyl ether, 1 part of triphenyl phosphite and 1 part of hypophosphorous acid. 102 parts of water were removed before the entrainer was removed by vacuum distillation. The product was purified through K 300 filter. The acid number was 26 mg of KOH/g and was adjusted to 99 mg of KOH/g by addition of 105 parts of acrylic acid. The viscosity of the almost colorless product (iodine color number 0–1) was 73.2 mPas.

Example 5

(About 15-tuply, Per Molecule of TMP, Ethoxylated TMP Triacrylate)

750 parts of 15-tuply ethoxylated trimethylolpropane (Emulan® TE15, BASF AG) were esterified with 216 parts of acrylic acid and 5 parts of sulfuric acid in 322 parts of methylcyclohexane. The assistants used were 3 parts of hydroquinone monomethyl ether, 1 part of triphenyl phosphite and 1 part of hypophosphorous acid. 44 parts of water were removed before the entrainer was removed by vacuum distillation. The product was purified through K300 filter. The acid number was 36 mg of KOH/g. The viscosity of the almost colorless product (iodine color number 0–1) was 324 mPas.

Example 6

(About 20-tuply, Per Molecule of TMP, Ethoxylated TMP Triacrylate)

830 parts of about 20-tuply ethoxylated trimethylolpropane were esterified with 216 parts of acrylic acid and 5 parts of sulfuric acid in 345 parts of methylcyclohexane. The assistants used were 3 parts of hydroquinone monomethyl ether, 1 part of triphenyl phosphite and 1 part of hypophosphorous acid. 44 parts of water were removed before the entrainer was removed by vacuum distillation. The product was purified through K300 filter. The acid number was 36 mg of KOH/g and was adjusted to 101 mg of KOH/g by addition of 96 parts of acrylic acid. The viscosity of the almost colorless product (iodine color number 0–1) was 324 mPas.

Example 7

(About 3-tuply, Per Glycerol Molecule, Ethoxylated Glycerol Triacrylate)

561 parts of about 3-tuply ethoxylated glycerol are esterified with 605 parts of acrylic acid and 5 parts of sulfuric acid in 390 parts of methylcyclohexane. The assistants used were 3 parts of hydroquinone monomethyl ether, 1.5 parts of triphenyl phosphite and 1.5 parts of hypophosphorous acid. 130 parts of water were removed before the entrainer was removed by vacuum distillation. The product was purified through K300 filter. The acid number was 30 mg of KOH/g. The viscosity of the almost colorless product (iodine color number 0–1) was 380 mPas.

Example 8

(About 5-tuply, Per Glycerol Molecule, Ethoxylated Glycerol Triacrylate)

940 parts of about 5-tuply ethoxylated glycerol (Lupranol® VP 9209, BASF Schwarzheide GmbH) were esterified with 670 parts of acrylic acid and 6 parts of sulfuric acid in 500 parts of methylcyclohexane. The assistants used were 3 parts of hydroquinone monomethyl ether, 1.5 parts of triphenyl phosphite and 1.5 parts of hypophosphorous acid. 44 parts of water were removed before the entrainer was removed by vacuum distillation. The product was purified through K300 filter. The acid number was 29 mg of KOH/g.

Example 9

(About 9-tuply, Per Glycerol Molecule, Ethoxylated Glycerol Triacrylate)

704 parts of about 9-tuply ethoxylated glycerol (Lutron® HF 1, BASF AG) were esterified with 363 parts of acrylic acid and 5 parts of sulfuric acid in 356 parts of methylcyclohexane. The assistants used were 3 parts of hydroquinone monomethyl ether, 1.5 parts of triphenyl phosphite and 1.5 parts of hypophosphorous acid. 76 parts of water were removed before the entrainer was removed by vacuum distillation. The product was purified through K300 filter. The acid number was 71 mg of KOH/g and was adjusted to 100 mg of KOH/g by addition of 8 parts of acrylic acid. The viscosity of the almost colorless product (iodine color number 0–1) was 113 mPas.

Example 10

(About 5-tuply, Per Molecule of Pentaerythritol, Ethoxylated Pentaerythritol Tetraacrylate)

382 parts of about 5-tuply ethoxylated pentaerythritol are esterified with 348 parts of acrylic acid and 5 parts of sulfuric acid in 180 parts of methylcyclohexane. The assistants used are 3 parts of hydroquinone monomethyl ether, 1.5 parts of triphenyl phosphite and 1.5 parts of hypophosphorous acid. 72 parts of water are removed before the entrainer is removed by vacuum distillation. The product is purified through K300 filter. The acid number is 35 mg of KOH/g. The viscosity of the dark-colored product (iodine color number not determinable) is 280 mPas.

Example 11

(About 13-tuply, Per Molecule, Ethoxylated Dipentaerythritol)

545 parts of about 13-tuply ethoxylated dipentaerythritol (DPP 130 from Perstorp AB) are esterified with 585 parts of acrylic acid and 5 parts of sulfuric acid in 400 parts of methylcyclohexane. The assistants used are 3 parts of hydroquinone monomethyl ether, 1.5 parts of triphenyl phosphite and 1.5 parts of hypophosphorous acid. 130 parts of water are separated off before the entrainer is separated off by vacuum distillation. The product is purified through K300 filter. The acid number is 45 mg of KOH/g. The viscosity of the slightly colored product (iodine color number 1–2) is 1600 mPas.

Example 12

(About 4-tuply, Per Molecule, Ethoxylated Sorbitol Acrylate)

490 parts of about 4-tuply ethoxylated sorbitol are esterified with 444 parts of acrylic acid and 5 parts of sulfuric acid in 448 parts of toluene. The assistants used are 3 parts of hydroquinone monomethyl ether, 1.5 parts of triphenyl phosphite and 1.5 parts of hypophosphorous acid. 96 parts of water are separated off before the entrainer is separated off by vacuum distillation. The product is purified through K300 filter. The acid number is 45 mg of KOH/g. The viscosity of the dark-colored product (iodine color number 3–4) is 990 mPas.

Example 13

(About 6-tuply, Per Molecule, Ethoxylated Sorbitol Acrylate)

601 parts of about 6-tuply ethoxylated sorbitol are esterified with 444 parts of acrylic acid and 5 parts of sulfuric acid in 448 parts of cyclohexane. The assistants used are 3 parts of hydroquinone monomethyl ether, 1.5 parts of triphenyl phosphite and 1.5 parts of hypophosphorous acid. 96 parts of water are separated off before the entrainer is separated off by vacuum distillation. The product is purified through K300 filter. The acid number is 45 mg of KOH/g. The viscosity of the dark-colored product (iodine color number 2–3) is 700 mPas.

Example 14

(About 8-tuply, Per Molecule, Ethoxylated Sorbitol Acrylate)

689 parts of about 8-tuply ethoxylated sorbitol are esterified with 444 parts of acrylic acid and 5 parts of sulfuric acid in 448 parts of toluene. The assistants used are 3 parts of hydroquinone monomethyl ether, 1.5 parts of triphenyl phosphite and 1.5 parts of hypophosphorous acid. 100 parts of water are separated off before the entrainer is separated off by vacuum distillation. The product is purified through K300 filter. The acid number is 45 mg of KOH/g. The viscosity of the dark-colored product (iodine color number 5) is 700 mPas.

Example 15

(About 10-tuply, Per Molecule, Ethoxylated Sorbitol Acrylate)

788 parts of about 8-tuply ethoxylated sorbitol are esterified with 444 parts of acrylic acid and 5 parts of sulfuric acid in 448 parts of toluene. The assistants used are 3 parts of hydroquinone monomethyl ether, 1.5 parts of triphenyl phosphite and 1.5 parts of hypophosphorous acid. 106 parts of water are separated off before the entrainer is separated off by vacuum distillation. The product is purified through K300 filter. The acid number is 45 mg of KOH/g. The viscosity of the dark-colored product (iodine color number 10–15) is 500 mPas.

Example 16

About 13-tuply, Per Molecule, Ethoxylated Sorbitol Hexaacrylate 625 parts of about 13-tuply ethoxylated sorbitol are esterified with 518 parts of acrylic acid and 5 parts of sulfuric acid in 381 parts of methyl cyclohexane. The assistants used are 3 parts of hydroquinone monomethyl ether, 1.5 parts of triphenyl phosphite and 1.5 parts of hypophosphorous acid. 116 parts of water are separated off before the entrainer is separated off by vacuum distillation. The product is purified through K300 filter. The acid number is 78 mg of KOH/g. The viscosity of the dark-colored product (iodine color number not determinable) is 406 mPas.

Making of Hydrogels

To determine the quality of surface crosslinking, the dried hydrogel can be investigated using the following test methods.

Test Methods a) Centrifuge Retention Capacity (CRC)

This method measures the free swellability of the hydrogel in a teabag. 0.2000±0.0050 g of dried hydrogel (particle size fraction 106–850 µm) are weighed into a teabag 60×85 mm in size which is subsequently sealed. The teabag is placed for 30 minutes in an excess of 0.9% by weight sodium chloride solution (at least 0.83 l/of sodium chloride solution/1 g of polymer powder). The teabag is then centrifuged for 3 minutes at 250 g. The amount of liquid is determined by weighing back the centrifuged teabag.

b) Absorbency Under Load (AUL) (0.7 psi)

The measuring cell for determining AUL-0.7 psi is a Plexiglass cylinder 60 mm in internal diameter and 50 mm in height. Adhesively attached to its underside is a stainless steel sieve bottom having a mesh size of 36 µm. The measuring cell further includes a plastic plate having a diameter of 59 mm and a weight which can be placed in the measuring cell together with the plastic plate. The plastic plate and the weight together weigh 1 345 g. AUL 0.7 psi is determined by determining the weight of the empty Plexiglass cylinder and of the plastic plate and recording it as $W_0$. 0.900±0.005 g of hydrogel-forming polymer (particle size distribution 150–800 µm) is then weighed into the Plexiglass cylinder and distributed very uniformly over the stainless steel sieve bottom. The plastic plate is then carefully placed in the Plexiglass cylinder, the entire unit is weighed and the weight is recorded as $W_a$. The weight is then placed on the plastic plate in the Plexiglass cylinder. A ceramic filter plate 120 mm in diameter and 0 in porosity is then placed in the middle of a Petri dish 200 mm in diameter and 30 mm in height and sufficient 0.9% by weight sodium chloride solution is introduced for the surface of the liquid to be level with the filter plate surface without the surface of the filter plate being wetted. A round filter paper 90 mm in diameter and <20 µm in pore size (S&S 589 Schwarzband from Schleicher & Schull) is subsequently placed on the ceramic plate. The Plexiglass cylinder containing hydrogel-forming polymer is then placed with plastic plate and weight on top of the filter paper and left there for 60 minutes. At the end of this period, the complete unit is removed from the Petri dish and subsequently the weight is removed from the Plexiglass cylinder. The Plexiglass cylinder containing swollen hydrogel is weighed together with the plastic plate and the weight recorded as $W_b$.

AUL was calculated by the following equation:

$$AUL0.7\ psi[g/g] = [W_b - W_a]/[W_a - W_0]$$

AUL 0.5 psi is measured in similar fashion at a lower pressure.

c) The 16 h extractables value is determined similarly to the description in EP-AL 811 636 at page 13 line 1 to line 19.

Examples 18–27

Making the Base Polymer

A Werner & Pfleiderer LUK 8.0 K2 laboratory kneader was charged with 6 kg of a 40% by weight aqueous acrylic acid solution which had been 77 mol % neutralized with sodium hydroxide.

The products reported in Table 1 were added in the amounts reported in Table 1, each based on acrylic acid used, as crosslinker. This was followed by the addition of 0.28% by weight of sodium persulfate and 0.0056% by weight of ascorbic acid, both percentages being based on acrylic acid monomer used, as polymerization initiator.

The reaction kicked off, and the temperature of the kneader shell was readjusted so that the heat of reaction was not removed via the shell. This creates almost adiabatic heating conditions for the reaction mixture, and the polymerization takes place with stirring. After the reaction has ended, the temperature is maintained for another hour or so. Thereafter, a finely crumbly gel was discharged in every case.

The gel was dried in a through air cabinet at 160° C. for 3 h, ground with a laboratory roll mill and sieved off at 100–850 micrometers. This is the normal base polymer of Table 1.

Alternatively, the gel was initially heated at 90° C. in a sealed plastic bag for 6 h and only then dried in a through air cabinet at 160° C. for 3 h, ground with a laboratory roll mill and finally sieved off at 100–850 micrometers. This is the hydrolyzed base polymer of Table 1.

Postcrosslinking:

The dry normal base polymer powder was sprayed with a solution of 0.06% by weight of ethylene glycol diglycidyl ether (from Nagase, Japan), 3.43% by weight of water and 1.47% by weight of 1,2-propanediol, each percentage being based on polymer used, and stirred until homogeneous. The moist powder was then heated at 150° C. in a drying cabinet for 60 min. Thereafter it was sieved once more at 850 micrometers to remove agglomerates. The properties of this postcrosslinked polymer were determined and are recited in Table 1.

TABLE 1

| Example | Crosslinker | Amount used | Solubility | Base polymer | | Postcrosslinked polymer | | |
|---|---|---|---|---|---|---|---|---|
| | | | | CRC | Extract. 16 h | CRC | AUL 0.7 psi | Extract. 16 h |
| 18 | Product of Example 1 | 0.44% | Clear | 36.2 | 9.9% | 27.9 | 25.8 | 7.2% |
| 19 | Product of Example 9 | 0.50% | Clear | 31.0 | 7.5% | 29.2 | 25.8 | 7.2% |
| 20 | Product of Example 4 | 0.50% | | 35.4 | 9.4% | 29.9 | 25.8 | 6.1% |
| 21 | Product of Example 5 | 0.50% | | 38.1 | 13.8% | 32.8 | 24.7 | 11.6% |
| 22 | Product of Example 6 | 0.50% | | 35.3 | 10.0% | 31.2 | 26.4 | 8.0% |

The solubility of the crosslinker was determined by adding the crosslinker to the reaction mixture at room temperature. Evaluation was by visual inspection.
The following scale was used:
Clear = complete clear solution
Cloudy = solution distinctly cloudy to the naked eye
Droplets = crosslinker separates in droplet form
The other products according to the present invention are convertible in a similar manner.

The invention claimed is:

1. A process for preparing a crosslinked hydrogel, which comprises
   a) reacting at least one polyalcohol A with at least one ethylenically unsaturated carboxylic acid B in the presence of at least one esterification catalyst C and of at least one polymerization inhibitor D and also optionally of a water-azeotroping solvent E to form an ester F,
   b) optionally removing some or all of the water formed in a) from the reaction mixture during and/or after a),
   f) optionally neutralizing the reaction mixture,
   h) optionally removing any solvent E by distillation and/or
   i) stripping with a reaction-inert gas,
   k) polymerizing the reaction mixture from one of a) to i), in the presence of at least one radical initiator K and of optionally at least one grafting base L, with optionally at least one additional monoethylenically unsaturated compound bearing no acid groups N and also optionally at least one further copolymerizable hydrophilic monomer M, wherein ester F acts as a crosslinker, whereby a crosslinked hydrogel is formed,
   l) optionally postcrosslinking the reaction mixture obtained from k),
   m) drying the reaction mixture obtained from k) or l), and
   n) optionally grinding and/or sieving the reaction mixture obtained from k), l) or m), wherein said ethylenically unsaturated carboxylic acid B is present in a molar excess to said polyalcohol A per hydroxyl group to be esterified in A of at least 2.5:1, and the optionally neutralized carboxylic acid B in the reaction mixture obtained after step i) substantially remains in said reaction mixture.

2. The process as claimed in claim 1, wherein not more than 75% by weight of said carboxylic acid B is removed from said reaction mixture obtained after the last of steps a) to i), said reaction mixture containing said ester F.

3. The process as claimed in claim 1, wherein said reaction mixture obtained after the last of steps a) to i), which comprises said ester F, has a DIN EN 3682 acid number of at least 25 mg of KOH/g.

4. The process as claimed in claim 1, wherein said reaction mixture obtained after the last of steps a) to i), which comprises said ester F, contains at least 0.5% by weight of said carboxylic acid B.

5. The process as claimed in claim 1, wherein said polyalcohol A is a polyol which comprises an additional functionality, said additional functionality being at least one ether, carboxyl or $C_1$–$C_4$-alkyloxycarbonyl function.

6. The process as claimed in claim 1, wherein said polyalcohol A is a polyol selected from the group consisting of ditrimethylolpropane, dipentaerythritol, dimethylolpropionic acid, dimethylolbutyric acid, and mixtures thereof.

7. The process as claimed in claim 1, wherein at least one polyalcohol A is selected from the group consisting of polyols, functionalized polyols, alkoxylated polyols, sugar alcohols, partially alkoxylated sugar alcohols, polyetherols, polyesterols, partially or fully alkoxylated polyesterols, partially or fully hydrolyzed alkoxylated polyesterols, and mixtures thereof.

8. The process as claimed in claim 1, wherein said polyalcohol A is a polyol which has been quadruply ethoxylated per hydroxyl group.

9. The process as claimed in claim 8, wherein said polyol is trimethylolpropane or pentaerythritol.

10. The process as claimed in claim 1, wherein said polyalcohol A is a from 3- to 4-tuply ethoxylated glycerol.

11. The process as claimed in claim 1, wherein said ester F in reaction step k) has a degree of esterification (based on the n-hydric polyalcohol A used) of at least 2 and less than n.

12. The process as claimed in claim 1, wherein said polyalcohol has the formula VIIa $$R^8\text{—}(O(CH(R^{10})CH(R^{10})O)_y\text{—}H)_x \qquad \text{(VIIa)},$$

where
R$^8$ is a polyvalent straight-chain or branched C$_2$–C$_{10}$-alkyl radical,
R$^{10}$ is independently in each occurrence hydrogen or methyl,
x is independently in each occurrence a positive integer of 2 or greater, and
y is independently in each occurrence a number from 3 to 8 for x=2 and a number from 2 to 7 for x=3 or greater.

13. The process as claimed in claim 12, wherein
R$_{10}$ is hydrogen and
y is independently in each occurrence a positive integer from 1 to 6 for each x.

14. The process as claimed in claim 12, wherein
R$_{10}$ is hydrogen and
y is independently in each occurrence a positive integer from 1 to 4 for each x.

15. The process as claimed in claim 12, wherein
R$_{10}$ is hydrogen and
y is independently in each occurrence a positive integer of more than 8 for x=2 and
y is independently in each occurrence a positive integer of more than 7 for x=3 or greater.

16. The process as claimed in claim 12, wherein
R$_{10}$ is hydrogen and
y is independently in each occurrence a positive integer of 15 or more for each x.

17. The process as claimed in claim 1, wherein the molar ratio of said at least one ethylenically unsaturated carboxylic acid B to said polyalcohol A in said reaction a) is at least 5:1, based on the hydroxyl groups of said polyalcohol A.

18. A crosslinked hydrogel comprising a copolymer obtained by crosslinking at least one hydrophilic monomer M or a copolymer thereof with a compound of the formula

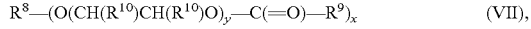 (VII), where
R$^8$ is a polyvalent straight-chain or branched C$_2$–C$_{10}$-alkyl radical,
R$^9$ is independently in each occurrence a straight-chain or branched C$_2$–C$_{10}$-alkenyl radical,
R$_{10}$ is independently in each occurrence hydrogen or methyl,
x is independently in each occurrence a positive integer of 2 or greater, and
y is independently in each occurrence a number greater than 8 for x=2 and a number greater than 7 for x=3 or greater.

19. A crosslinked hydrogel comprising a copolymer obtained by crosslinking at least one hydrophilic monomer M or a copolymer thereof with an ester F of a polyalcohol A with at least one ethylenically unsaturated carboxylic acid B, said polyalcohol A being selected from the group consisting of a polyol which comprises an additional functionality, said additional functionality being at least one carboxyl or C$_1$–C$_4$-alkyloxycarbonyl function, sugar alcohols, partially alkoxylated sugar alcohols, polyesterols, partially or fully alkoxylated polyesterols and partially or fully hydrolyzed alkoxylated polyesterols.

20. A crosslinked hydrogel comprising a copolymer obtained by crosslinking at least one hydrophilic monomer M or a copolymer thereof with an ester F of a polyalcohol A with at least one ethylenically unsaturated carboxylic acid B, said polyalcohol A being selected from the group consisting of ditrimethylolpropane, dipentaerythritol, dimethylolpropionic acid and dimethylolbutyric acid.

21. A crosslinked hydrogel comprising at least one hydrophilic monomer M in interpolymerized form, crosslinked with a reaction mixture comprising an ester F of a polyalcohol A with at least one ethylenically unsaturated carboxylic acid B, said reaction mixture being obtained by reaction of a polyalcohol A with at least one
a) ethylenically unsaturated carboxylic acid B in the presence of at least one esterification catalyst C and of at least one polymerization inhibitor D and also optionally of a water-azeotroping solvent E to form an ester F,
b) optionally removing some or all of the water formed in a) from the reaction mixture during and/or after a),
f) optionally neutralizing the reaction mixture,
h) optionally removing any solvent E by distillation and/or
i) stripping with a reaction-inert gas,
wherein
said ethylenically unsaturated carboxylic acid B is present in a molar excess to said polyalcohol A per hydroxyl group to be esterified in A of at least 2.5:1, and
the optionally neutralized carboxylic acid B in the reaction mixture obtained after the last step substantially remains in said reaction mixture.

22. The process as claimed in claim 1, wherein said ethylenically unsaturated carboxylic acid B is present in a molar excess to said polyalcohol A per hydroxyl group to be esterified in A of at least 5:1.

23. The process as claimed in claim 1, wherein said ethylenically unsaturated carboxylic acid B is present in a molar excess to said polyalcohol A per hydroxyl group to be esterified in A of at least 100:1.

24. The process as claimed in claim 1, wherein excess ethylenically unsaturated carboxylic acid B is not substantially removed after the last steps a) to i).

25. The process as claimed in claim 1, wherein excess esterification catalyst C is not substantially removed after the last steps a) to i).

26. The process as claimed in claim 1, wherein the polymerization inhibitor is an aerobic polymerization inhibitor.

27. The process as claimed in claim 1, wherein step k) is carried out in a protective, nitrogen gas containing atmosphere.

28. The process as claimed in claim 1, wherein radical initiator K is a peroxide or an azo compound.

29. The process as claimed in claim 1, wherein step k) is carried out with an ester F concentration of 0.01–5% by weight, based on the amount of polymerizable monomers present.

30. The process as claimed in claim 29, wherein the concentration is 0.1–0.75% by weight.

* * * * *